United States Patent
Tsukada et al.

(10) Patent No.: US 10,472,598 B2
(45) Date of Patent: Nov. 12, 2019

(54) CELL MASS CULTURE VESSEL

(71) Applicant: SUMITOMO BAKELITE CO., LTD., Shinagawa-ku (JP)

(72) Inventors: Ryohei Tsukada, Tokyo (JP); Haruo Okubo, Tokyo (JP)

(73) Assignee: SUMITOMO BAKELITE CO., LTD., Shinagawa-ku (JP)

( * ) Notice: Subject to any disclaimer, the term of this patent is extended or adjusted under 35 U.S.C. 154(b) by 0 days.

(21) Appl. No.: 15/310,224

(22) PCT Filed: May 20, 2015

(86) PCT No.: PCT/JP2015/064444
§ 371 (c)(1),
(2) Date: Nov. 10, 2016

(87) PCT Pub. No.: WO2015/178413
PCT Pub. Date: Nov. 26, 2015

(65) Prior Publication Data
US 2017/0267960 A1    Sep. 21, 2017

(30) Foreign Application Priority Data

May 22, 2014 (JP) .................. 2014-106450
Oct. 27, 2014 (JP) .................. 2014-218661

(51) Int. Cl.
*B01L 3/00* (2006.01)
*C12M 1/00* (2006.01)
(Continued)

(52) U.S. Cl.
CPC .......... *C12M 23/12* (2013.01); *B01L 3/5085* (2013.01); *C12M 23/20* (2013.01); *C12N 1/00* (2013.01);
(Continued)

(58) Field of Classification Search
CPC ............ B01L 3/5085; B01L 2200/028; B01L 2200/0647; B01L 2300/0829;
(Continued)

(56) References Cited

U.S. PATENT DOCUMENTS 5,514,343 A * 5/1996 Verwohlt .............. B01L 3/5085
                                                        211/74
5,578,490 A    11/1996 Martinez Ubeira
(Continued)

FOREIGN PATENT DOCUMENTS

CN    101815782 A    8/2010
JP    7-115958 A     5/1995
(Continued)

OTHER PUBLICATIONS

Chen et al. "Microfluidic array for three-dimensional perfusion culture of human mammary epithelial cells" Biomed Microdevices (2011) 13:753-758 (Year: 2011).*
(Continued)

*Primary Examiner* — Liban M Hassan
(74) *Attorney, Agent, or Firm* — Oblon, McClelland, Maier & Neustadt, L.L.P.

(57) ABSTRACT

A cell aggregate culture vessel (1) is a vessel for culturing a cell aggregate. The cell aggregate culture vessel (1) includes a well (21) having a culture space capable of storing the cell aggregate and culture fluid and a tubular body (3) which is disposed on the well on a plane at which the well has an opening and have an inner cavity communicating with the culture space, and one or more communication portion (3a) capable of discharging the culture fluid without allowing passage of the cell aggregate to the outside of the tubular body (3) is formed in a tubular wall of the tubular
(Continued)

body (3). The communication portion (3a) may be, for example, a slit having a width of 0.1 mm or larger and 0.5 mm or smaller.

24 Claims, 21 Drawing Sheets

(51) Int. Cl.
    *C12M 1/32* (2006.01)
    *C12N 1/00* (2006.01)
    *C12N 5/09* (2010.01)

(52) U.S. Cl.
    CPC ...... *C12N 5/0693* (2013.01); *B01L 2200/028* (2013.01); *B01L 2200/0647* (2013.01); *B01L 2300/0829* (2013.01); *B01L 2300/0851* (2013.01)

(58) Field of Classification Search
    CPC ........... B01L 2300/0851; C12M 23/12; C12M 23/20; C12N 5/0693; C12N 1/00
    USPC ....................................... 435/289.1
    See application file for complete search history.

(56) References Cited

U.S. PATENT DOCUMENTS

| | | |
|---|---|---|
| 9,121,003 B2 | 9/2015 | Nakazawa et al. |
| 2007/0207537 A1* | 9/2007 | Cui ........................ C12M 23/12 435/288.4 |
| 2008/0003672 A1 | 1/2008 | Cecchi et al. |
| 2010/0009442 A1 | 1/2010 | Sasai et al. |
| 2010/0068793 A1* | 3/2010 | Ungrin .................. B01L 3/5085 435/283.1 |
| 2010/0190253 A1 | 7/2010 | Tazaki et al. |
| 2011/0003389 A1 | 1/2011 | Nakazawa et al. |
| 2013/0122580 A1* | 5/2013 | Tsukada ................. C12M 23/12 435/289.1 |
| 2014/0011269 A1 | 1/2014 | Sakura et al. |
| 2015/0140652 A1 | 5/2015 | Sasai et al. |

FOREIGN PATENT DOCUMENTS

| | | |
|---|---|---|
| JP | 7-203946 A | 8/1995 |
| JP | 2003-57157 A | 2/2003 |
| JP | 2008-99662 A | 5/2008 |
| JP | 2008-178367 A | 8/2008 |
| WO | 2007/049576 A1 | 5/2007 |
| WO | 2008/156041 A1 | 12/2008 |
| WO | 2012/133514 A1 | 10/2012 |
| WO | 2013/183777 A1 | 12/2013 |

OTHER PUBLICATIONS

Furusawa et al., "English machine translation of JP 2003-057157". (Year: 2003).*

Tokushige Nakano, et al., "Self-Formation of Optic Cups and Storable Stratified Neural Retina from Human ESCs", Cell Stem Cell, vol. 10, pp. 771-785, (Jun. 14, 2012).

International Search Report dated Aug. 18, 2015 in PCT/JP15/64444 Filed May 20, 2015.

\* cited by examiner

CELL MASS CULTURE VESSEL

TECHNICAL FIELD

The present disclosure relates to a cell aggregate culture vessel and a cell aggregate culture method using the same. Priority is claimed on Japanese Patent Application No. 2014-106450, filed May 22, 2014, and Japanese Patent Application No. 2014-218661, filed Oct. 27, 2014, the contents of which are incorporated herein by reference.

BACKGROUND ART

Embryonic stem cells (ES cells) have multilineage potential and can differentiate into a variety of tissue cells. Therefore, a variety of studies have been carried out relating to the application of embryonic stem cells in the field of so-called regenerative medicine, in which cells lost due to disease, accidents, or the like are repaired and tissues are restored (for example, PTL 1).

ES cells have great diversity and can differentiate into a variety of cells. An example of a method for differentiating ES cells into a variety of cells is the formation of cell aggregates known as embryonic bodies (EB). These cell aggregates are formed by floating a culture of ES cells, iPS cells, and the like, and, when the ES cells are cultured for approximately two weeks in a state in which cell aggregates are formed, differentiation into a variety of cell types is observed. Therefore, the formation of embryonic bodies is used as one of the standard methods for investigating the pluripotent differentiation of cells.

Among the methods for culturing ES cells in a floating state, the most widely used method is hanging drop culture. Hanging drop culture is a method in which cells are cultured in culture fluids suspended in a water droplet shape. However, this method has problems of a low success rate of formation of embryonic bodies, incapability of microscopic observation, troublesome operations, and the like. In order to solve these problems, for example, culture vessels having water-insoluble cured membranes formed on the vessel inner surfaces by curing water-soluble resin membranes have been proposed (for example, PTL 2).

When clinical application is considered, research and development using human ES cells becomes necessary, but human ES cells have problems of a higher possibility of cell death and a greater difficulty in obtaining embryonic bodies compared with mouse ES cells. In order to solve these problems, for example, culture vessels have been proposed in which funnel shapes having an aperture angle in a range of 60 degrees to 100 degrees are provided as the well bottom portions and the center portions have concave roundness (for example, PTL 3). For research and development using human iPS cells as well, the same culture vessels have been proposed.

PTL 1 (Japanese Unexamined Patent Application, First Publication No. 2008-99662), PTL 2 (Japanese Unexamined Patent Application, First Publication No. 2008-178367), and PTL 3 (WO2013/183777) are incorporated into the present specification by reference.

CITATION LIST

Patent Literature

[PTL 1] Japanese Unexamined Patent Application, First Publication No. 2008-99662

[PTL 2] Japanese Unexamined Patent Application, First Publication No. 2008-178367

[PTL 3] WO2013/183777

Non-Patent Literature

[NPL 1] Cell Stem Cell, Vol. 10, No. 6, pp. 771 to 785 (2012)

SUMMARY OF INVENTION

Technical Problem

There are cases in which cell aggregates formed using the above-described culture vessels are moved to Schale or the like for additional culture (NPL 1). Generally, waste products such as uric acid or carbon dioxide discharged from cells make culture fluids acidic, and thus culture fluids in Schale need to be exchanged periodically. However, when Schale is shaken due to such periodic exchange of culture fluids, there is a concern that cell aggregates may accumulate in the center portion of the Schale and come into contact and fuse with each other, and thus, the cell aggregates may become too large or may have distorted shapes, oxygen or nutrients may not be sufficiently supplied to cells constituting the cell aggregates, and the cells may die. In addition, even normal cells are damaged due to enzymes and the like released from the dead cells. Therefore, in culturing, it is important to grow cell aggregates up to appropriate diameters and exchange culture fluids while causing minimal damage or exposure to stimuli in order to obtain high-quality cell aggregates through culture. In addition, since stem cells, for example, human embryonic stem cells (human ES cells) or human pluripotent stem cells (human iPS cells), have a favorable metabolism, the exchange frequency of culture fluids is higher than that in other cells. Therefore, particularly for these cells, efficient exchange of culture fluids is desired.

In one or a plurality of embodiments, the present disclosure provides a culture vessel which has little influence on cell aggregates and is capable of efficiently exchanging culture fluids, and a cell aggregate culture method using the same.

Solution to Problem

In one or a plurality of embodiments, the present disclosure relates to a vessel for culturing cell aggregates. The cell aggregate culture vessel includes a well having a culture space capable of storing the cell aggregates and culture fluids and a tubular body having an inner cavity communicating with the culture space, and one or more communication portion capable of discharging the culture fluids without allowing passage of the cell aggregates to the outside of the tubular body are formed in a tubular wall of the tubular body.

In one or a plurality of embodiments, the present disclosure is a culture method for culturing cell aggregates using the cell aggregate culture vessel of the present disclosure. The cell aggregate culture method includes a step of culturing the cell aggregates in the well in which the culture space is filled with culture fluids, and thereafter inclining the cell aggregate culture vessel, thereby passing some of the culture fluids in the well through the communication portion and discharging the culture fluids to the outside of the tubular body.

Advantageous Effects of Invention

According to the cell aggregate culture vessel and the cell aggregate culture method of the present disclosure, there is little influence on cell aggregates, and culture fluids can be efficiently exchanged with each other.

DESCRIPTION OF EMBODIMENTS

Figure 1A:
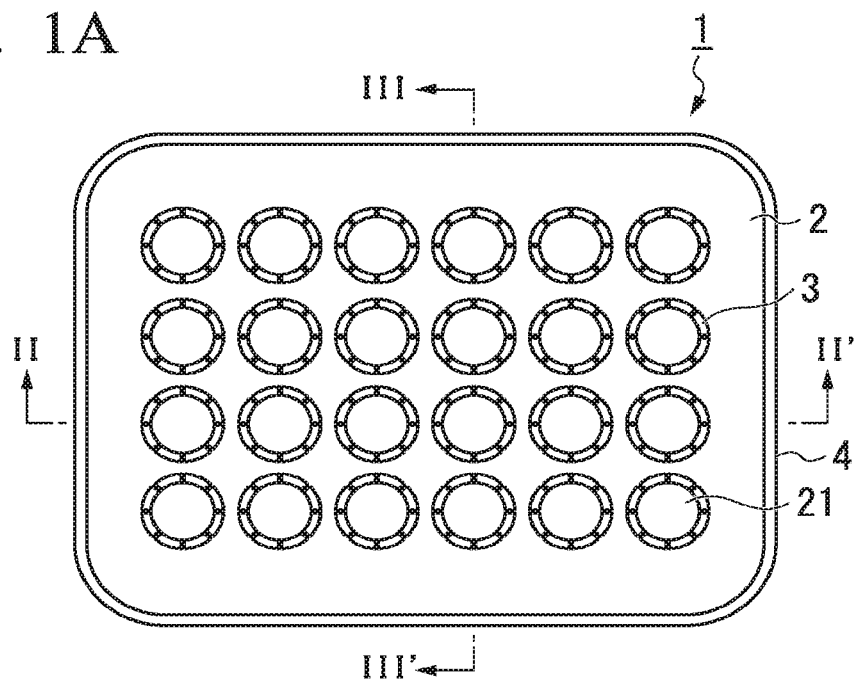
FIG. 1A is a plan view of a cell aggregate culture vessel of Embodiment 1.

A cell aggregate culture vessel of the present disclosure (hereinafter, in some cases, also abbreviated as the "culture vessel") has inner cavities communicating with culture spaces in wells and includes a tubular body in which one or more communication portion capable of discharging culture fluids without allowing passage of cell aggregates to the outside are formed in a tubular wall thereof. Therefore, with a simple operation of inclining the culture vessel, it is possible to discharge culture fluids in a plurality of the wells from the culture space within a short period of time. When culture fluids are discharged using the above-described method, compared with the methods described in the related art, culture fluids can be efficiently exchanged with each other without adversely affecting cell aggregates. Since culture fluids in a plurality of the wells can be discharged from the culture spaces, automatic exchange of culture fluids using machines can also be expected.

Among cells, stem cells such as human embryonic stem cells (human ES cells) or human pluripotent stem cells (human iPS cells) have favorable metabolism and have a possibility of being differentiated due to slight stimuli. Therefore, the culture vessel of the present disclosure capable of efficiently exchanging culture fluids while suppressing the influence of damage, stimuli, and the like on cell aggregates is suitable for culture of cell aggregates of these stem cells.

The present disclosure relates to the following one or a plurality of embodiments.

(1) A cell aggregate culture vessel for culturing a cell aggregate, including: a well having a culture space capable of storing the cell aggregate and culture fluid and a tubular body which is disposed on the well on a plane at which the well has an opening and has an inner cavity communicating with the culture space, in which one or more communication portion capable of discharging the culture fluid without allowing passage of the cell aggregate to the outside of the tubular body is formed in a tubular wall of the tubular body.

(2) The cell aggregate culture vessel according to (1), in which a plurality of the communication portions are formed in the tubular body.

(3) The cell aggregate culture vessel according to (1) or (2), in which the communication portion is a slit parallel to a central axis of the tubular body.

(4) The cell aggregate culture vessel according to (1) or (2), in which the communication portion is a slit along a circumferential direction of the tubular body.

(5) The cell aggregate culture vessel according to (3) or (4), in which widths of the slit is 0.1 mm or larger and 0.5 mm or smaller.

(6) The cell aggregate culture vessel according to any one of (3) to (5), in which, in a case in which a structure made up of the well and the tubular body is cut on a plane including a central axis thereof and is seen in plan view, a length from one of both ends of the slit which is closer to the well to the deepest portion of the well is 3.0 mm or larger and 6.0 mm or smaller.

(7) The cell aggregate culture vessel according to any one of (1) to (6), in which the cell aggregate culture vessel includes a multi-well plate body including a plurality of the wells, and a plurality of the tubular bodies are disposed on the well on the plane at which the wells of the multi-well plate have openings.

(8) The cell aggregate culture vessel according to (7), in which the communication portion is a slit which is parallel to the central axes of the tubular body and are formed from base end of the tubular body.

(9) The cell aggregate culture vessel according to (7) or (8), in which the multi-well plate body and the plurality of tubular bodies are molded in the same mold.

(10) The cell aggregate culture vessel according to any one of (1) to (6), in which the cell aggregate culture vessel includes a multiwell plate body including a plurality of the wells and a side wall which protrudes above the opening of the well so as to surround the plurality of wells and has a substantially rectangular shape when seen in plan view and a liquid flow control body disposed in a space surrounded by the side wall of the multi-well plate, the liquid flow control body includes the plurality of tubular bodies, a plurality of crosslinking portions which are disposed so as not to come into contact with a surface of the multi-well plate body which has the opening of the well and connect the plurality of tubular bodies so as to form a connected body of the plurality of tubular bodies, and at least a pair of position-regulating portions having one end portion connected to the connected body and the other end portion coming into contact with the side wall, and one position-regulating portion comes into contact with one of the inner surfaces of the side wall which face each other, and the other position-regulating portion comes into contact with the other of the inner surfaces of the side wall which face each other.

(11) The cell aggregate culture vessel according to (10), in which the liquid flow control body is a separate body from the multi-well plate body.

(12) The cell aggregate culture vessel according to any one of (1) to (11), further including: a liquid guide portion, in which the liquid guide portion includes a pair of protrusion portions disposed on an inner surface of the structure made up of the well and the tubular body, the protrusion portions form a liquid guide assisting groove, and upper side end surfaces of the protrusion portions are disposed above lower side end of the communication portion.

(13) The cell aggregate culture vessel according to (12), in which surfaces of the protrusion portions facing the culture space are curved surfaces protruding toward the central axes of the tubular body.

(14) The cell aggregate culture vessel according to (12) or (13), in which a length from the upper side end surfaces of the protrusion portions to the lower side end of the communication portion is 0.1 mm or larger.

(15) The cell aggregate culture vessel according to any one of (12) to (14), in which a distance between a pair of the protrusion portions on a circumference passing through the lower side end of the communication portion is 0.3 mm or larger and 1.0 mm or smaller.

(16) The cell aggregate culture vessel according to any one of (12) to (15), in which lower side end portions of the protrusion portions reach a bottom surface in the inner surface of the well.

(17) The cell aggregate culture vessel according to any one of (12) to (16), in which the liquid guide portion connects the lower side end portions of a pair of the protrusion portions together and further includes a base portion including a surface defining one terminating end of the liquid guide assisting groove.

(18) The cell aggregate culture vessel according to (17), in which the surface defining one terminating end of the liquid guide assisting groove is an inclined surface inclining from a downstream side to an upstream side of a flow of the culture fluid capable of flowing from the communication portion into the culture space.

(19) The cell aggregate culture vessel according to any one of (12) to (18), in which closed end of the liquid guide assisting groove is disposed above a bottom portion of the well.

(20) The cell aggregate culture vessel according to any one of (1) to (19), in which at least an inner surface of the bottom portion of the well is coated with a coating layer formed of a water-soluble resin represented by Formula (Ia) or (Ib) below

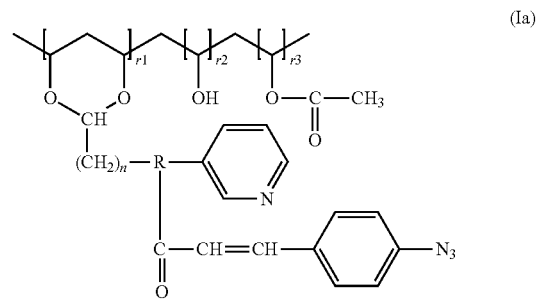

(In Formula (Ia), R represents a hydrocarbon group having a carbonyl group and a —NH— group, r1 represents 1 to 1,000, r2 represents 40 to 4,995, r3 represents 0 to 4,000, and n represents 1, 2, or 3)

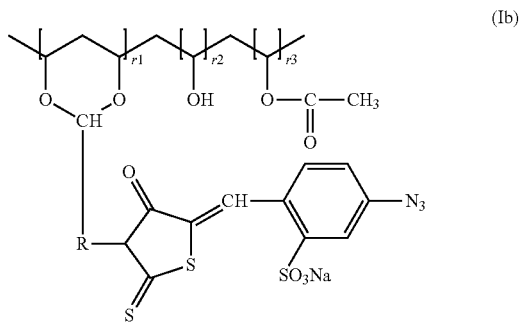

(In Formula (Ib), R represents a hydrocarbon group having a carbonyl group and a —NH— group, r1 represents 1 to 1,000, r2 represents 40 to 4,995, and r3 represents 0 to 4,000).

(21) The cell aggregate culture vessel according to any one of (1) to (20), in which the well has a tubular trunk portion and a funnel-shaped bottom portion provided at one end of the trunk portion, a central portion of the bottom portion is a concave surface, an aperture angle of the bottom portion is in a range of 60 degrees to 100 degrees, and a curvature radius of the concave surface of the bottom portion is in a range of 0.5 mm to 2.0 mm.

(22) The cell aggregate culture vessel according to any one of (1) to (21), in which the cell aggregate is stem cells.

(23) The cell aggregate culture vessel according to (22), in which the stem cells are human embryonic stem cells (human ES cells) or human pluripotent stein cells (human iPS cells).

(24) A cell aggregate culture method for culturing a cell aggregate using the cell aggregate culture vessel according to any one of (1) to (23), including a step of culturing the cell aggregate in the well in which the culture space is filled with culture fluid, and thereafter inclining the cell aggregate culture vessel, thereby passing some of the culture fluid in the well through the communication portion and discharging the culture fluid to the outside of the tubular body.

[1] A cell aggregate culture vessel for culturing cell aggregates, including: a well having a culture space capable of storing the cell aggregates and culture fluids, a tubular body having an inner cavity communicating with the culture space, and a liquid guide portion, in which one or more communication portion capable of discharging the culture fluids without allowing passage of the cell aggregates to the outside of the tubular body is formed in a tubular wall of the tubular body, the liquid guide portion including a liquid guide assisting groove, provided by forming a pair of protrusion portions on an inner surface of a structure made up of the well and the tubular body, and disposing an upper side end surface of each of the protrusion portions above lower side end of the communication portion, and forming one of the protrusion portion at each of both sides of at least one communication portion on an inner surface of the tubular portion.

[2] The cell aggregate culture vessel according to [1], in which the communication portion is a slit parallel to a central axis of the tubular body.

[3] The cell aggregate culture vessel according to [2], in which the slit is formed from a base end of the tubular body.

[4] The cell aggregate culture vessel according to [2] or [3], in which widths of the slit is 0.1 mm or larger and 0.5 mm or smaller.

[5] The cell aggregate culture vessel according to any one of [1] to [4], in which surfaces of the respective protrusion portions which face the culture space are curved surfaces protruding toward the central axis of the tubular body.

[6] The cell aggregate culture vessel according to any one of [1] to [5], in which a length from upper side end surfaces of the protrusion portions to lower side end of the communication portion is 0.1 mm or larger.

[7] The cell aggregate culture vessel according to any one of [1] to [6], in which a distance between the protrusion portions on a circumference passing through the lower side end of the communication portion is 0.3 mm or larger and 1.0 mm or smaller.

[8] The cell aggregate culture vessel according to any one of [1] to [7], in which lower side end portions of the respective protrusion portions reach a bottom surface in the inner surface of the well.

[9] The cell aggregate culture vessel according to any one of [1] to [7], in which the liquid guide portion connects the lower side end portions of the respective protrusion portions together and further includes a base portion including a surface defining one terminating end of the liquid guide assisting groove.

[10] The cell aggregate culture vessel according to [9], in which the surface defining one terminating end of the liquid guide assisting groove is an inclined surface inclining from a downstream side to an upstream side of a flow of the culture fluid capable of flowing from the communication portion into the culture space.

[11] The cell aggregate culture vessel according to any one of [1] to [10], in which, in a case in which the structure made up of the well and the tubular body is cut on a plane including a central axis thereof and is seen in plan view, a length from the lower side end of the communication portion to the deepest portion of the well is 3.0 mm or larger and 6.0 mm or smaller.

[12] The cell aggregate culture vessel according to any one of [1] to [11], in which the well has a tubular trunk portion and a funnel-shaped bottom portion provided at one end of the trunk portion, a central portion of the bottom portion is a concave surface, an aperture angle of the bottom portion is in a range of 60 degrees to 100 degrees, and a curvature radius of the concave surface of the bottom portion is in a range of 0.5 mm to 2.0 mm.

[13] The cell aggregate culture vessel according to [12], in which a closed end of the liquid guide assisting groove is disposed above the bottom portion of the well.

[14] The cell aggregate culture vessel according to any one of [1] to [13], in which the cell aggregate culture vessel includes a multi-well plate body including a plurality of the wells, and a plurality of the tubular bodies are disposed on a surface of the multi-well plate which has the openings of the wells.

[15] The cell aggregate culture vessel according to [14], in which the multi-well plate body and the plurality of tubular bodies are molded in the same mold.

[16] The cell aggregate culture vessel according to [12] or [13], in which at least an inner surface of the bottom portion of the well is coated with a coating layer formed of a water-soluble resin represented by Formula (Ia) or (Ib) below

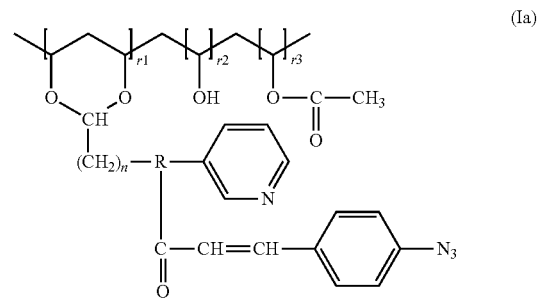

(Ia)

(In Formula (Ia), R represents a hydrocarbon group having a carbonyl group and a —NH— group, r1 represents 1 to 1,000, r2 represents 40 to 4,995, r3 represents 0 to 4,000, and n represents 1, 2, or 3.)

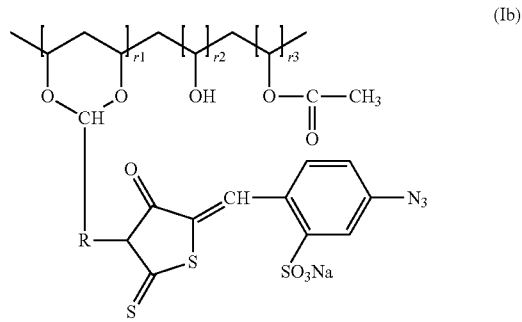

(Ib)

(In Formula (Ib), R represents a hydrocarbon group having a carbonyl group and a —NH— group, r1 represents 1 to 1,000, r2 represents 40 to 4,995, and r3 represents 0 to 4,000.)

[17] The cell aggregate culture vessel according to any one of [1] to [16], in which the cell aggregates are stem cells.

[18] The cell aggregate culture vessel according to [17], in which the stem cells are human embryonic stem cells (human ES cells) or human pluripotent stem cells (human iPS cells).

[19] A cell aggregate culture method for culturing cell aggregates using the cell aggregate culture vessel according to any one of [1] to [18], including a step of culturing the cell aggregates in the well in which the culture space is filled with culture fluids, and thereafter inclining the cell aggregate culture vessel, thereby passing some of the culture fluids in the well through the communication portion and discharging the culture fluids to the outside of the tubular body.

Hereinafter, embodiments of the present invention will be described in detail with reference to the accompanying drawings. In the drawings, the same or similar portions will be assigned the same or corresponding reference signs and will not be described again. Dimensional ratios in the respective drawings are, in some cases, exaggerated for description in some portions and do not necessarily coincide with actual dimensional ratios.

Embodiment 1

Figure 1B:
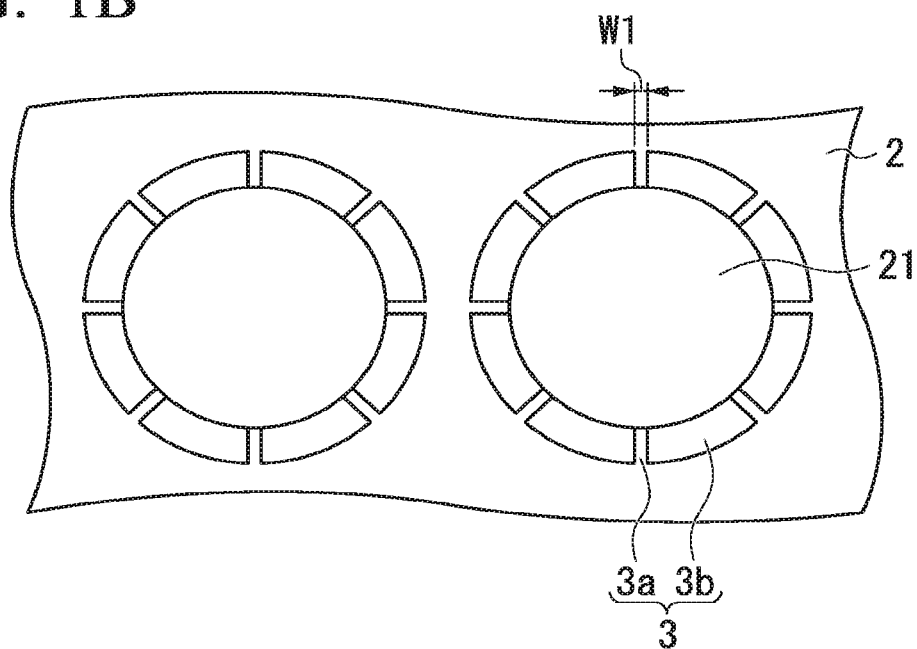
FIG. 1B is a partial enlarged view of FIG. 1A.
Figure 2:
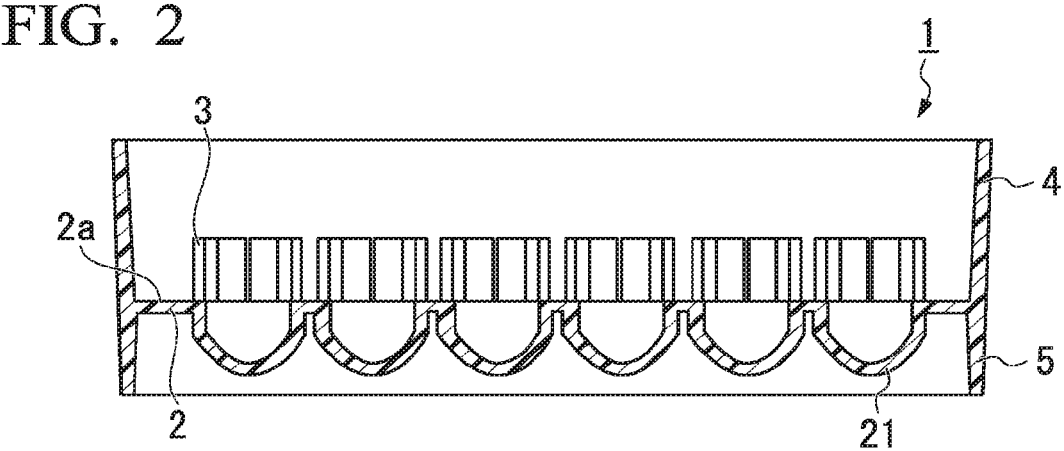
FIG. 2 is a sectional view in the direction of arrow line II-II' in FIG. 1A.
Figure 3:
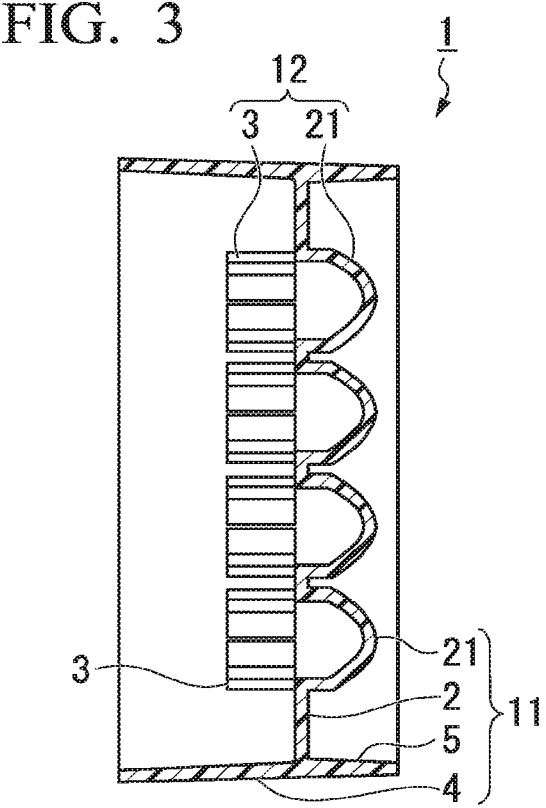
FIG. 3 is a sectional view in the direction of arrow line in FIG. 1A.
Figure 4:
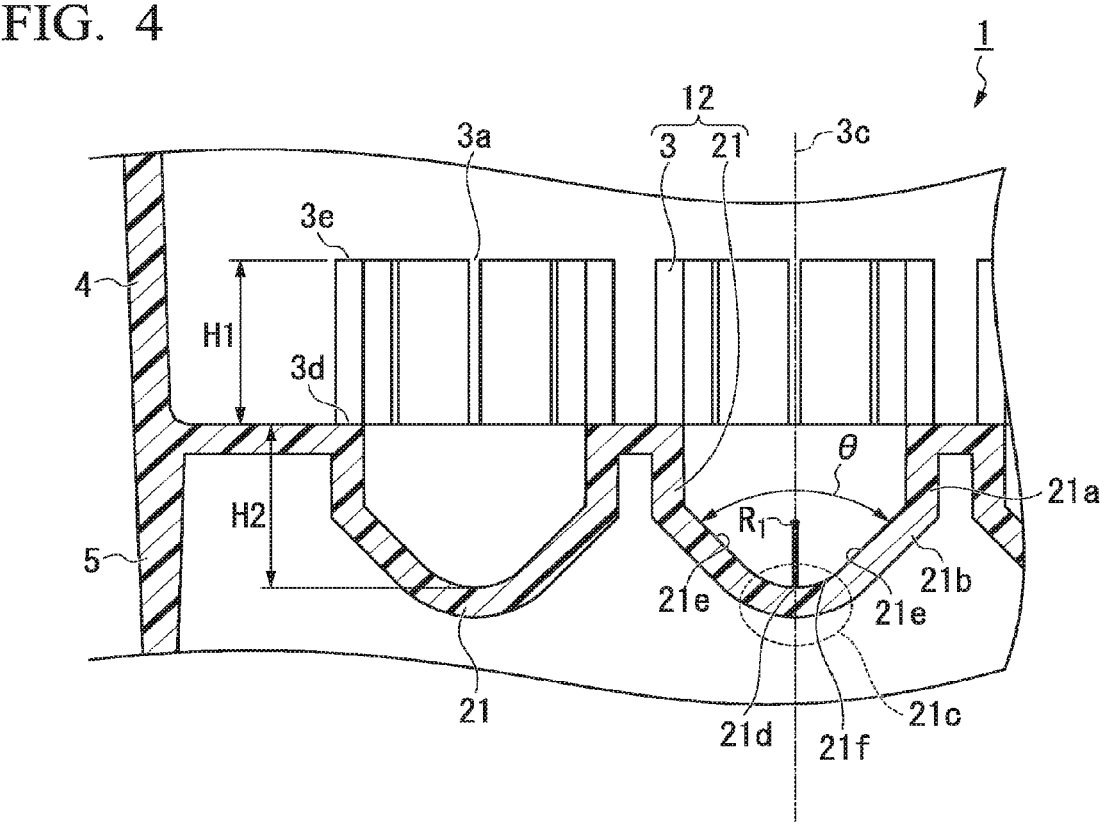
FIG. 4 is a partial enlarged view of FIG. 2.

FIG. 1A is a plan view of a cell aggregate culture vessel of Embodiment 1, and FIG. 1B is a partial enlarged view of FIG. 1A. FIG. 2 is a sectional view in the direction of arrow line II-II' in FIG. 1A, FIG. 3 is a sectional view in the direction of arrow line in FIG. 1A, and FIG. 4 is a partial enlarged view of FIG. 2.

A culture vessel 1 of Embodiment 1 which will be described using FIGS. 1A to 4 is a vessel for culturing cell aggregates. The culture vessel 1 includes a plurality of wells 21 formed in a plate-like body 2 and tubular bodies 3 disposed above the respective wells 21. For convenience, a direction intersecting the plane of the plate-like body 2 at right angles will be referred to as the "vertical direction", the tubular body 3 side will be referred to as being "above", and the well 21 side will be referred to as being "below".

The culture vessel 1 of Embodiment 1 includes a side wall 4 which protrudes above openings of a plurality of the wells 21 and surrounds a plurality of the wells 21 and a base 5 which protrudes below the openings of a plurality of the wells 21. The shapes of the outer surface and the inner surface of the side wall 4 when the culture vessel 1 is seen in plan view are substantially rectangular respectively. The base 5 protrudes further than the wells 21 from the plate-like body 2, and thus, when the culture vessel 1 is placed on a horizontal surface, the end surface of the base 5 comes into contact with the horizontal surface.

The respective wells 21 have a culture space capable of storing a cell aggregate and culture fluid. The tubular body 3 has a substantially cylindrical shape and has an inner cavity communicating with the culture space. In a tubular wall 3b of the tubular body 3, a plurality of communication portions 3a are formed at equal intervals along the circumferential direction of the tubular body 3. The communication portion 3a is a slit which is parallel to a central axis 3c (refer to FIG. 4) of the tubular body 3 and is formed from a base end 3d to a front end 3e of the tubular body 3. Furthermore, the central axis 3c of the tubular body 3 is parallel to the vertical direction.

In an example of the culture vessel 1 of Embodiment 1 which will be described using FIGS. 1A to 4, one end of both ends of the slit 3a which is closer to the well 21 coincides with the base end 3d of the tubular body 3, and the other end further from the well 21 coincides with the front end 3e of the tubular body 3. However, slits are not limited to the above-described example as long as, when the culture vessel 1 is inclined in order to discharge some of the culture fluids, some of the culture fluids in the wells 21 can be appropriately discharged without allowing cell aggregates to exit from the wells 21. For example, a slit may be formed toward the front ends 3e of the tubular bodies 3 from above the base ends 3d of the tubular bodies 3. Alternatively, a slit may be a through-hole which penetrate the tubular walls of the tubular bodies 3 in the thickness direction thereof and have the longitudinal direction along the circumferential direction of the tubular bodies 3. Alternatively, the communication portion 3a is not limited to a slit and may be, for example, a through hole penetrating the tubular walls 3b of the tubular bodies 3 in the thickness direction thereof.

In an example of the culture vessel 1 of Embodiment 1 which will be described using FIGS. 1A to 4, the number of the communication portions 3a (slits) is eight, but there is no particular limitation regarding the number of the communication portions 3a. However, the number of the communication portions is preferably two or more, more preferably four or more, and still more preferably six or more since it is easy to efficiently discharge culture fluids from the respective wells 21 and fresh culture fluids described below are allowed to easily and uniformly move into the respective wells. In addition, in a case in which each of the wells 21 includes two or more communication portions 3a, the angle between a pair of the communication portions 3a selected from the two or more communication portions 3a which are separated from each other in the circumferential direction is preferably 90 degrees or more and more preferably 180 degrees or more since culture fluids are efficiently discharged.

As illustrated in FIG. 1B, any width W1 (the width in the circumferential direction) of the slit is acceptable as long as the width is smaller than the diameter of the cell aggregate measured by microscopic observation just before the cell aggregate is moved to the culture vessel 1 of Embodiment 1. When the diameter of the cell aggregate is in a range of 600 μm to 700 μm, the width is preferably 0.1 mm or larger, more preferably 0.2 mm or larger, and still more preferably 0.25 mm or larger from the viewpoint of improvement in the discharge efficiency of culture fluids, and the width is preferably 0.5 mm or smaller, more preferably 0.4 mm or smaller, and still more preferably 0.3 mm or smaller, in order to reduce the possibility of cell aggregates flowing out.

In the present specification, in a case in which the longitudinal direction of the slit is parallel to the central axis 3c (refer to FIG. 4) of the tubular body 3, the width of the slit refers to the length of the slit in a direction perpendicular to the central axis 3c (refer to FIG. 4) of the tubular body 3. In addition, in a case in which the longitudinal direction of the slit is along the circumferential direction of the tubular body 3, the width of the slit refers to the length of the slit in a direction parallel to the central axis 3c (refer to FIG. 4) of the tubular body 3.

In a cell aggregate culture method of the present disclosure described below, the liquid surface of culture fluids is preferably placed above the base ends 3d of the tubular bodies 3 in order for the quality of culture fluids in a plurality of the wells 21 to be made uniform by means of diffusion using the communication portions 3a. In the culture method, the height H1 of the tubular body 3 is preferably in a range of 1 mm to 7 mm and more preferably in a range of 3 mm to 5 mm so as to prevent cell aggregates from floating on culture fluids, exceeding the front end of the tubular body 3, and moving into a space between the tubular body 3 and the side wall 4, adjacent tubular bodies 3, and adjacent wells 21.

The openings (apertures) of a plurality of the wells 21 are in the same plane as one surface 2a (refer to FIG. 2) of the plate-like body 2 connecting a plurality of the wells 21 together, and the tubular bodies 3 are disposed on the plane. The slits which are the communication portion 3a are preferably formed from the base ends 3d (refer to FIG. 4) of the tubular bodies 3 from the viewpoint of improvement in the discharge efficiency of culture fluids.

In order to suppress physical stimuli from being applied to cell aggregates in the middle of the discharging of culture fluids, it is preferable that there are no levels on the inner surface of a structure 12 (refer to FIGS. 3 and 4) made up of the tubular bodies 3 and the wells 21, and specifically, it is preferable that the central axes 3c of the tubular bodies 3 coincide with the central axes of the wells 21 and the radii of cylindrical surfaces which are the inner circumferential surfaces of the tubular bodies 3 are equal to the radii of the openings of the wells 21. In addition, in a case in which, for example, the well 21 includes a tubular trunk portion 21a (refer to FIG. 4) and the inner surface of the trunk portion 21a is a cylindrical surface, it is preferable that the central axes 3c of the tubular bodies 3 coincide with the central axes of the wells 21 and the radii of the cylindrical surfaces which are the inner circumferential surfaces of the tubular bodies 3 are equal to the radii of the cylindrical surfaces which are the inner circumferential surfaces of the trunk portions 21a.

Each of the wells 21 includes the tubular trunk portion 21a and a funnel-shaped bottom portion 21b provided at one end of the trunk portion 21a. In the bottom portion 21b, the culture space in the well 21 contracts toward the front end (opposite to the opening) of the well 21. In the inner surface facing the culture space in the well 21, a central portion 21c of the bottom portion is a curved surface. That is, the inner surface of the bottom portion 21b can be an inverted conic surface having a curved surface at the top portion. The trunk portion 21a may have, for example, a substantially cylindrical shape. In one or a plurality of embodiments of each of the wells 21, in a sectional view (refer to FIG. 4) of the well 21 cut on a plane including the central axis thereof, the inner surface of the bottom portion 21b has a substantially V shape and is arcuate in the central portion 21c. In one or a plurality of embodiments of each of the wells 21, a continuous portion between the trunk portion 21a and the bottom portion 21b in the inner surface is preferably a curved surface.

In addition, in one or a plurality of embodiments, in a case in which the well 21 is cut on a plane including the central axis thereof and is seen in plan view, the inner surface of the well 21 is substantially parallel to the central axis of the well 21 in the trunk portion 21a, includes a pair of inclined surfaces 21e inclining toward a central axis passing through a top point 21d (the deepest portion) of the inner surface of the well 21 in the funnel-shaped bottom portion 21b, and includes an arcuate surface 21f in the central portion 21c of the bottom portion 21b.

As illustrated in FIG. 4, the aperture angle θ of the bottom portion 21b is preferably greater than 60 degrees and 100 degrees or smaller, more preferably in a range of 70 degrees to 100 degrees, and still more preferably in a range of 80 degrees to 90 degrees since it is possible to efficiently culture cell aggregates. The "aperture angle" in the present disclosure refers to the angle formed by the pair of inclined surfaces 21e and is, for example, the angle indicated by θ in FIG. 4.

The curvature radius $R_1$ on the central portion inner surface of the bottom portion 21b is preferably in a range of 0.5 mm to 2.0 mm since, during the exchange of culture fluids, cell aggregates are not exposed on the surface of culture fluids and stimuli being applied to cell aggregates can be suppressed and is more preferably in a range of 1.0 mm to 2.0 mm since it is easy to observe cell aggregates using an optical microscope. Furthermore, in the present specification, the "curvature radius of the central portion inner surface" refers to a radius corresponding to a circumference including a curved surface in which the curvature of the front end portion of the bottom portion 21b of the well 21 is $1/R_1$. The curvature radius $R_1$ of the central portion inner surface can be measured using laser distance meters or by means of actual measurements of cut sections of molded products.

In a case in which the structure 12 (refer to FIG. 4) made up of the wells 21 and the tubular bodies 3 is cut on a plane including the central axis thereof and is seen in plan view, the length 112 (refer to FIG. 4) from one end of both ends of the slit 3a which is closer to the well 21 to a deepest portion 21d of the well 21 is preferably in a range of 3.0 mm to 6.0 mm since, after some of the culture fluids are removed in order to exchange culture fluids, cell aggregates to which new culture fluids are yet to be added are not exposed on the surface of culture fluids and damage or stimuli being applied to cell aggregates due to the removal of culture fluids are reduced and is more preferably in a range of 3.0 mm to 5.0 mm since, furthermore, a sufficient amount of nutrients and oxygen are supplied to cell aggregates.

In a case in which the slit 3a is formed toward the front end 3e of the tubular body 3 from the base end 3d of the tubular body 3, the depth of the well 21 is preferably in a range of 3.0 mm to 6.0 mm since, after some of the culture fluids are removed in order to exchange culture fluids, cell aggregates to which new culture fluids are yet to be added are not exposed on the surface of culture fluids and damage or stimuli being applied to cell aggregates due to the removal of culture fluids are reduced and is more preferably in a range of 3.0 mm to 5.0 mm since, furthermore, a sufficient amount of nutrients and oxygen are supplied to cell aggregates.

The diameter of the well 21 at the opening is, for example, preferably 4.0 mm or larger since operability is excellent in a case in which multi dispensers are used and is preferably 11.0 mm or smaller since the number of the wells 21 per culture vessel increases.

The capacity of the structure 12 (refer to FIG. 4) made up of the wells 21 and the tubular bodies 3 per inside space, in other words, the sum of the capacity of the culture spaces of the wells 21 (the inside spaces of the wells 21) and the capacity of the inside spaces in the inner circumferential surfaces (for example, cylindrical surfaces) of the tubular bodies 3 is not particularly limited, but is, for example, preferably in a range of 50 μL to 500 μL since a sufficient amount of culture fluids or reagents can be added in order to culture cell aggregates and is more preferably in a range of 50 μL to 200 μL since the amount of culture fluids or reagents being used decreases.

Furthermore, the form of the well in the culture vessel of the present embodiment is not limited to the well including the trunk portion 21a and the funnel-shaped bottom portion 21b. The form of the well may be, for example, a form in which the inner surface has a hemispherical shape or a form in which a trunk portion and a bottom portion are provided and the bottom portion has a hemispherical shape as long as it is possible to discharge some of the culture fluids in wells without allowing cell aggregates to exit from the wells.

In one or a plurality of embodiments, a cell adhesiveness reduction treatment is preferably carried out on at least the inner surface of the bottom portion 21b of the well 21. In the present disclosure, the "cell adhesiveness reduction treatment" refers to a treatment for reducing the adhesiveness of the inner surface of the well 21 to cells. Adhesiveness being reduced means that, for example, it becomes difficult for the inner surface of the well 21 and cells to adhere to each other or the inner surface of the well 21 and cells become incapable of adhering to each other.

Examples of the cell adhesiveness reduction treatment include hydrophilization treatments on the inner surfaces of the wells 21. Examples of the hydrophilization treatments include formation of coating layers using water-soluble resins, formation of coating layers using hydrophilic resins, and the like. In the present disclosure, "water-soluble resins" refers to resins which are hydrated by means of ionic bonding or hydrogen bonding with water molecules and are thus dissolved in water and have a solubility of 1.0 g or higher in 100 g of water at 25° C. In addition, examples of the water-soluble resins include resins having a necessary and sufficient amount of ionic or polar side chains with respect to main chains in molecules in order to be dissolved in water.

Examples of the water-soluble resins include saponified substances of polyvinyl acetates, polyvinylpyrrolidone, polyethylene glycols, polyacrylamides, polymethacrylamides, polyhydroxyethylmethacrylates, polypentaerythritol triacrylates, polypentaerythritol tetraacrylates, polydiethylene glycol diacrylates, copolymers of monomers constituting the above-described water-soluble resins, copolymers between 2-methacryloyloxyethyl phosphorylcholine and other monomers (for example, butyl methacrylates and the like), and the like. Among these, structures made up of one or more selected from saponified substances of polyvinyl acetates, polyvinylpyrrolidone, and polyethylene glycols and functional groups described below are preferred. The above-described structures can suppress stimuli on a variety of cells and improve the growth rates of cell aggregates and the qualities of grown cell aggregates.

Examples of the saponified substances of polyvinyl acetates include copolymers between polyvinyl alcohols or vinyl alcohols and other compounds, saponified substances between hydrophilic group-modified, hydrophobic group-modified, anionic modified, cationic modified, or amide group-modified vinyl acetates or modified vinyl acetates obtained by modifying reactive groups such as acetoacetyl groups, and the like. The average degree of polymerization of polymers is not particularly limited, but is preferably in a range of 100 to 10,000 and more preferably in a range of 200 to 5,000 since it is easy to form uniform membranes on the inner surfaces of culture vessels and workability becomes favorable. The degree of saponification of the saponified substances of polyvinyl acetates is not particularly limited, but is preferably in a range of 20 mol % to 100 mol % and more preferably in a range of 50 mol % to 95 mol % of the entire polyvinyl acetates.

The water-soluble resins are preferably water-soluble resins having functional groups to be cured in side chains. Examples of the functional groups to be cured include radioactive reactive, photosensitive, and thermal reactive functional groups and the like. Examples of the photosensitive functional groups include diazo groups, azide groups, cinnamoyl groups, and the like. Examples of the thermal reactive and radioactive reactive functional groups include vinyl groups, epoxy groups, and the like. Among water-soluble resins having these functional groups, water-soluble resins having photosensitive functional groups are preferred since it is possible to rapidly carry out curing treatments and cure the functional groups using simple facilities.

The water-soluble resins are preferably water-soluble resins having azide groups and more preferably water-soluble resins represented by Formula (Ia) or (Ib) below since it is possible to form uniform coating layers by means of irradiation with light having wavelengths in a range of 300 nm to 500 nm and improve the growth efficiency of cell aggregates by reducing the amount of cells adhered.

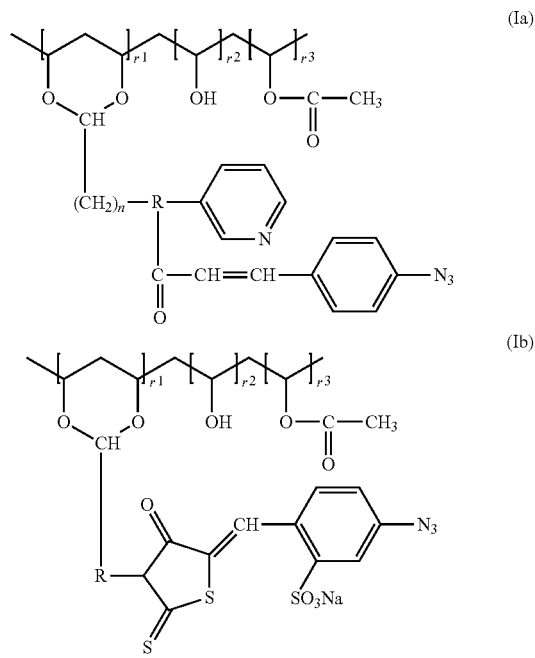

In Formula (Ia), R represents a trivalent hydrocarbon group having a carbonyl group and a —NH— group. Examples of the hydrocarbon group include saturated hydrocarbon groups and unsaturated hydrocarbon groups, and, among these, groups represented by Formula (II) below are preferred since it becomes easy to synthesize polar side chains.

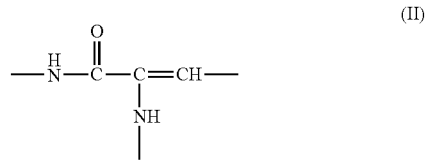

In Formula (Ib), R represents a divalent hydrocarbon group having a carbonyl group and a —NH— group. Examples of the hydrocarbon group include saturated hydrocarbon groups and unsaturated hydrocarbon groups.

In Formula (Ia), r1 represents 1 to 1,000, r2 represents 40 to 4,995, r3 represents 0 to 4,000, and n represents 1, 2, or 3. In Formula (Ib), r1 represents 1 to 1,000, r2 represents 40 to 4,995, and r3 represents 0 to 4,000.

The hydrophilic resins are not particularly limited, and examples thereof include poly-2-hydroxyethyl methacrylate (poly-HEMA), phosphocholine group-containing polymer compounds, polyethylene glycol chain-containing polymer compounds, and the like.

The thickness of the coating layer is not particularly limited, but is, for example, preferably in a range of 100 nm to 5,000 nm and more preferably in a range of 150 nm to 1,000 nm since it is possible to suppress cells being adhered to the wells through protein by reducing the amount of protein incorporated into the coating layer while reducing physical stimuli received by cells from the base material (the wells).

Materials for the culture vessel according to the present disclosure are not particularly limited, but are preferably resins since it is possible to make the culture vessel disposable and molding is easy. Examples of the resins include polyolefin-based resins or cyclic polyolefin-based resins such as polypropylene resins, polyethylene resins, and ethylene-propylene copolymers, polystyrene-based resins such as polystyrene, acrylonitrile-butadiene-styrene-based resins, methacryl-based resins such as polycarbonate resins, polyethylene terephthalate resins, and polymethyl methacrylate resins, fluorine-based resins such as vinyl chloride resins, polybutylene terephthalate resins, polyacrylate resins, polyarylate resins, polysulphone resins, polyether sulphone resins, polyether ether ketone resins, polyether imide resins, and polytetrafluoroethylene, cellulose-based resins such as propionate resins, and the like. Among these, polystyrene resins are preferred from the viewpoint of moldability and sterilizing properties, which are required in culture vessels.

Examples of the form of the culture vessel according to the present disclosure include multi-well plates including a plurality of wells and the like. The number of wells in the multi-well plate is not particularly limited and is, for example, 6, 12, 24, 48, 96, or 384.

The culture vessel according to the present disclosure can be manufactured in the following manner.

First, the above-described resin material is molded into a desired shape by means of injection molding, blow molding, injection blow molding, or the like. In the culture vessel 1 of Embodiment 1 which is shown using FIGS. 1A to 4, a multi-well plate body 11 including the plate-like body 2, a plurality of the wells 21 formed in the plate-like body 2, the side wall 4, and the base 5 and a plurality of the tubular bodies 3 can be molded in the same mold using an injection molding method.

Next, the cell adhesiveness reduction treatment is carried out on the formed vessel. The cell adhesiveness reduction treatment can be carried out using, for example, the method described in WO2013/183777.

After the above-described cell adhesiveness reduction treatment, the vessel is sterilized. Examples of the sterilization include ethylene oxide gas sterilization, hot air sterilization, irradiation sterilization, and the like, irradiation sterilization using γ rays or electron beams is preferred, and γ ray sterilization is more preferred from the viewpoint of radiotransparency when aggregate production is taken into account.

[Cell Aggregate Culture Method]

Next, a method for culturing cell aggregates using the culture vessel of the present disclosure will be described. According to the cell aggregate culture method according to the present disclosure (hereinafter, in some cases, also abbreviated as the "culture method"), since the culture vessel according to the present disclosure is used, there is little influence on cell aggregates, and culture fluids can be efficiently exchanged with each other, and thus cell aggregates can be efficiently cultured.

In one or a plurality of embodiments, the culture method of the present disclosure includes a culture fluid exchange step of culturing cell aggregate in the well in which the culture spaces are filled with culture fluid for a predetermined time, and thereafter inclining the cell aggregate culture vessel according to the present disclosure, thereby passing some of the culture fluid in the well through the communication portion so as to discharge the culture fluid to the outside of the tubular body, then, removing the culture fluid from the culture vessel, and then adding the same amount or almost the same amount of new culture fluid (fresh culture fluid) as the removed culture fluid to the culture vessel, and the culture fluid exchange step is repeated a predetermined number of times.

In a case in which the culture subjects of the culture method of the present disclosure are, for example, cell aggregates of human embryonic stem cells (human ES cells) or human pluripotent stem cells (human iPS cells), it is also possible to, for example, move cell aggregates formed in the multi-well plate for forming cell aggregates to the culture vessel of the present disclosure together with the full amount of culture fluids and apply the culture method of the present disclosure to the cell aggregates. The diameters of cell aggregates which are formed in the multi-well plate for forming cell aggregates and are soon to be moved to the culture vessel of the present disclosure (that is, cell aggregates which become the subject of culture using the culture vessel of the present disclosure) observed by means of microscopic observation is preferably in a range of 500 μm to 1,000 μm since a sufficient amount of nutrients can be supplied to cell aggregates in the culture vessel of the present disclosure. Cell aggregates are moved to the culture vessel of the present disclosure so that one cell aggregate is disposed in one well.

In the culture fluid exchange step, the "predetermined time" may vary depending on the kinds of cells, the capacity of the wells, the purpose of culture, and the like and may vary every culture fluid exchange step. For example, the "predetermined time" in the culture fluid exchange step in the beginning of culture may be longer than the "predetermined time" in the culture fluid exchange step performed later than the beginning of the culture. In addition, the number of times of the culture fluid exchange step is also appropriately determined depending on the kinds of cells, the capacity of the wells, the purpose of the culture, and the like.

In the culture fluid exchange step, some of the culture fluids in the respective wells are made to pass through the communication portions and are discharged to the outside of the tubular bodies in order to reduce damage or stimuli applied to cell aggregates due to the removal of culture fluids. After some of the culture fluids are removed and before new culture fluids are added, cell aggregates are preferably held in a state in which cell aggregates are all sunk in the culture fluids.

In the culture fluid exchange step, the amount of culture fluids being removed from the culture vessel and the amount of new culture fluids being added are preferably in a range of 50 parts by aggregate to 99 parts by aggregate and more preferably in a range of 75 parts by aggregate to 99 parts by aggregate when the amount of culture fluids in the culture vessel which are soon to be removed is considered as 100 parts by aggregate since cell aggregates are not exposed on the surface of culture fluids and a sufficient amount of nutrients and oxygen are supplied to cell aggregates due to the addition of fresh culture fluids.

In the culture fluid exchange step, the culture vessel is preferably shaken so that, after new culture fluids are added to the culture vessel, the fresh culture fluids uniformly move into the respective wells.

As culture fluids that are used in the culture fluid exchange step, culture fluids that have been thus far well-known may be used depending on the kinds of cells, the capacity of the wells, the purpose of culture, and the like.

In the culture method of the present disclosure, as long as cell aggregates do not excessively float and thus exit from the wells 21, culture fluids are preferably supplied not only to the culture spaces in the wells 21 but also to the space which is above the openings of the wells 21 and is surrounded by the side wall 4 since the qualities of culture fluids in a plurality of the wells 21 are made uniform by means of diffusion through the communication portions 3a. In other words, culture fluids are preferably supplied so that some of the culture fluids spill out of a plurality of the wells 21 and are loaded into even the inner cavities of the tubular bodies 3 on the base end side. The liquid surface of the culture fluids may be above one ends of both ends of the slits 3a which are closer to the wells 21.

Cell aggregates that have been subjected to the cell aggregate culture method in which the culture vessel of the present disclosure is used may be moved to another culture vessel and be further cultured in the culture vessel.

Embodiment 2

Figure 5:
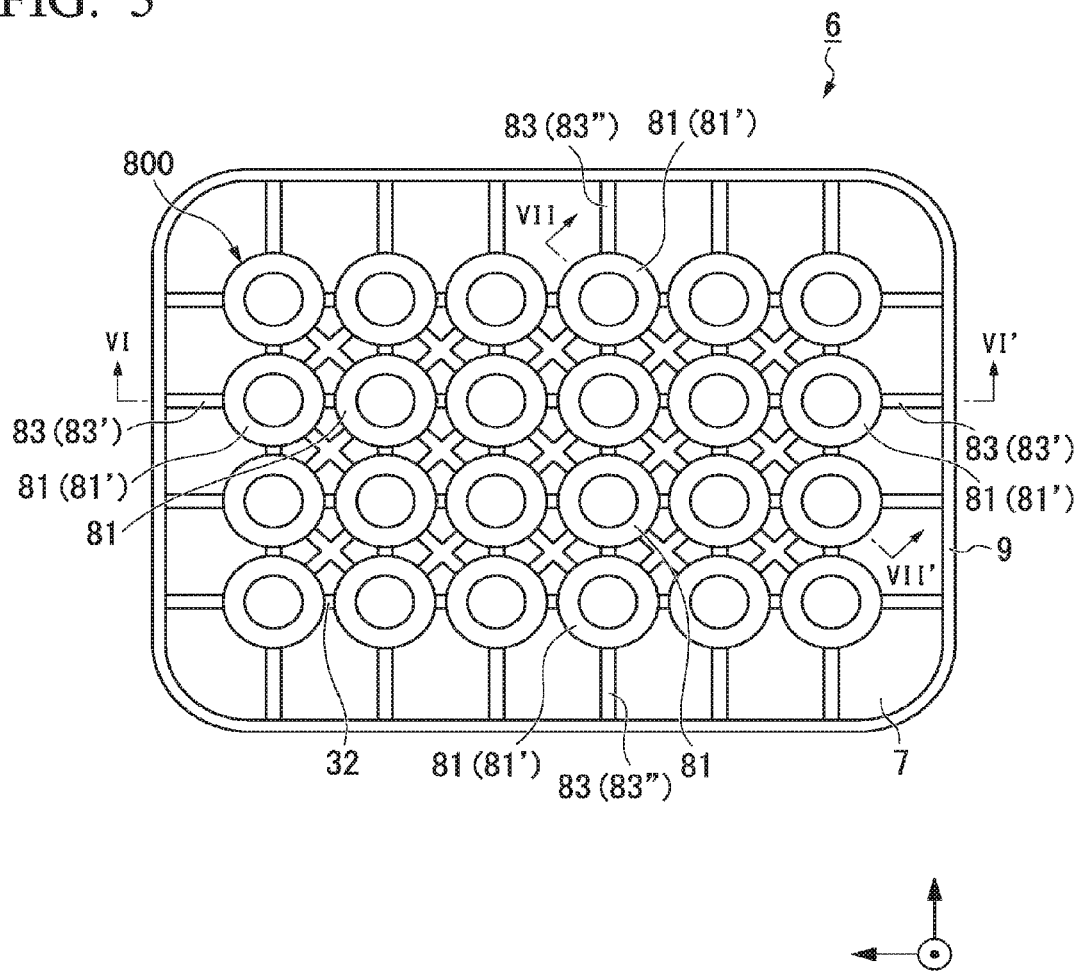
FIG. 5 is a plan view of a cell aggregate culture vessel of Embodiment 2.
Figure 6:
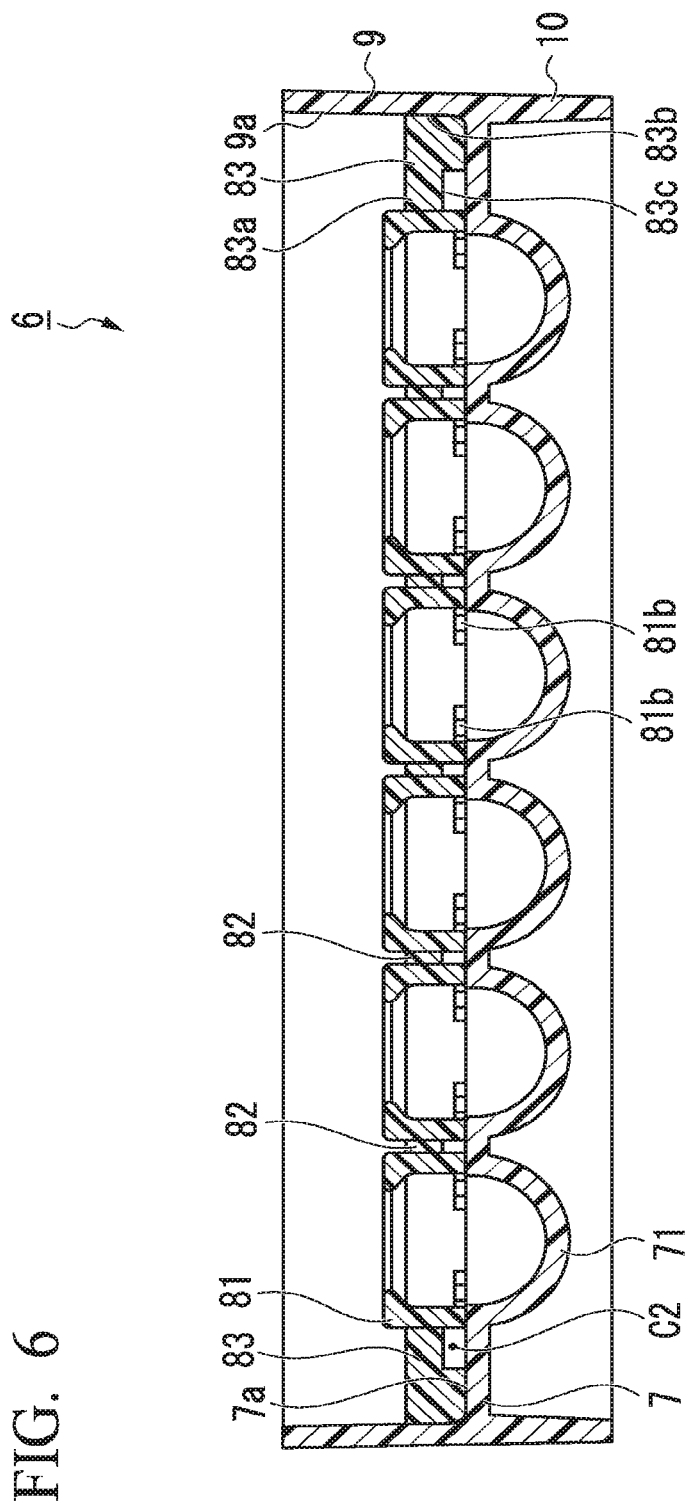
FIG. 6 is an enlarged sectional view in the direction of arrow line VI-VI' in FIG. 5.
Figure 7:
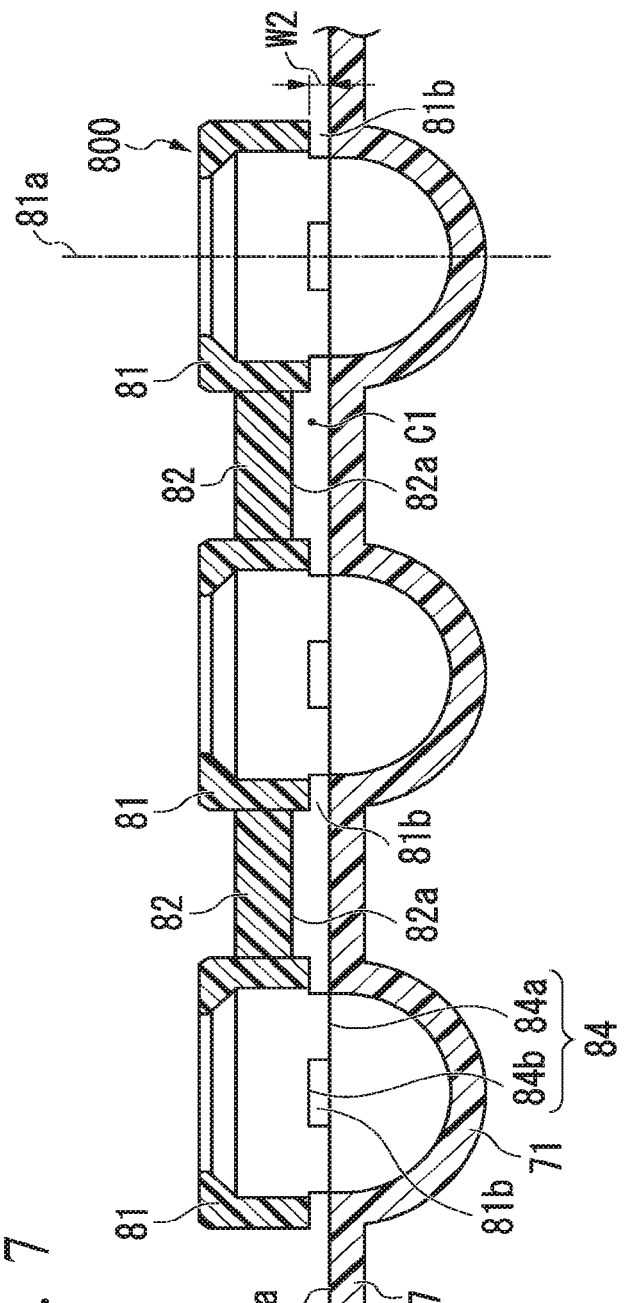
FIG. 7 is an enlarged end view cut in the direction of arrow line VII-VII' in FIG. 5.
Figure 8:
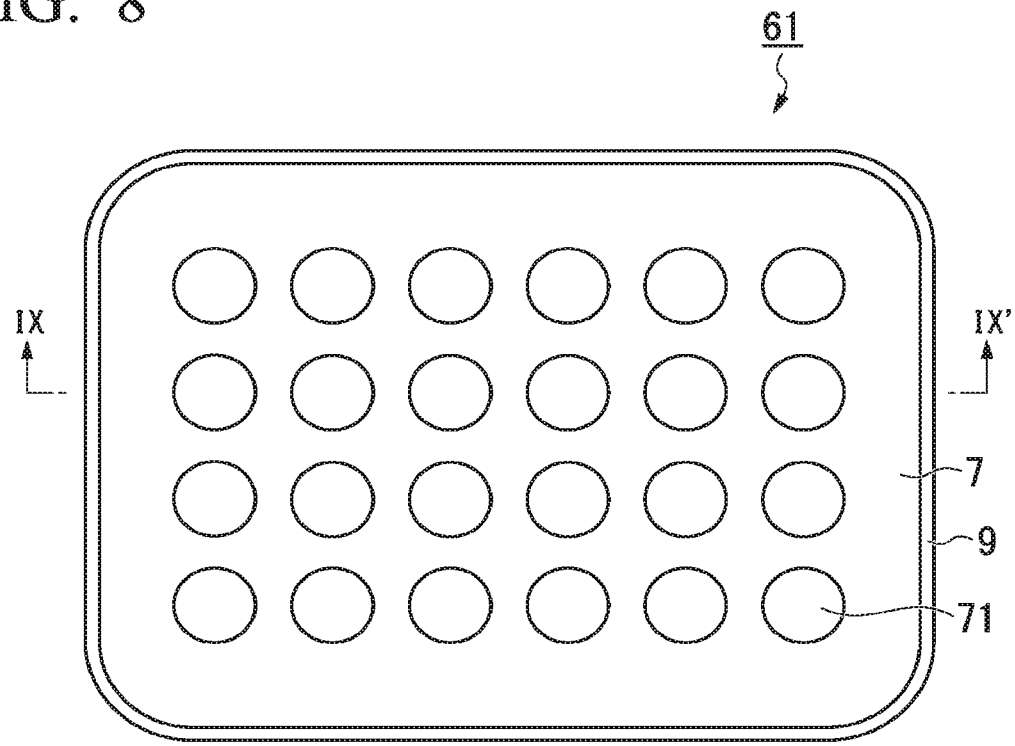
FIG. 8 is a plan view of a multi-well plate body constituting the cell aggregate culture vessel of Embodiment 2.
Figure 9:
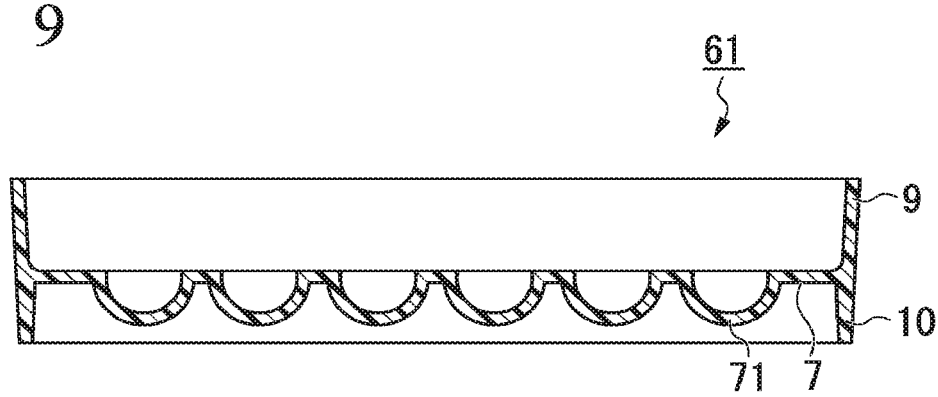
FIG. 9 is a sectional view in the direction of arrow line IX-IX' in FIG. 8.
Figure 10:
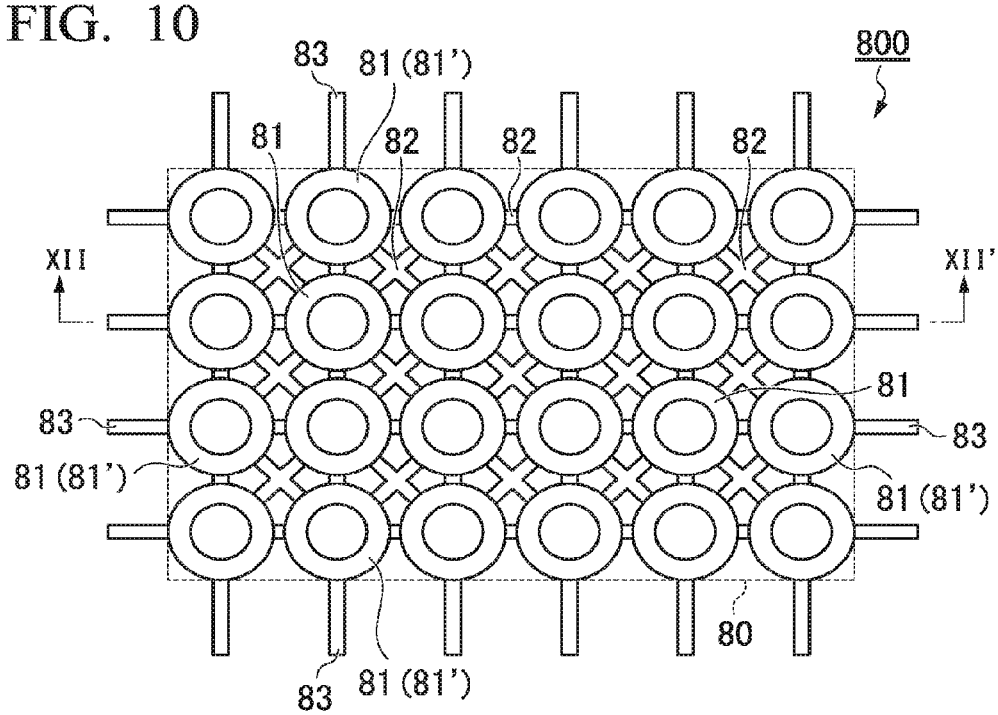
FIG. 10 is a plan view of a liquid flow control body constituting the cell aggregate culture vessel of Embodiment 2.
Figure 12:
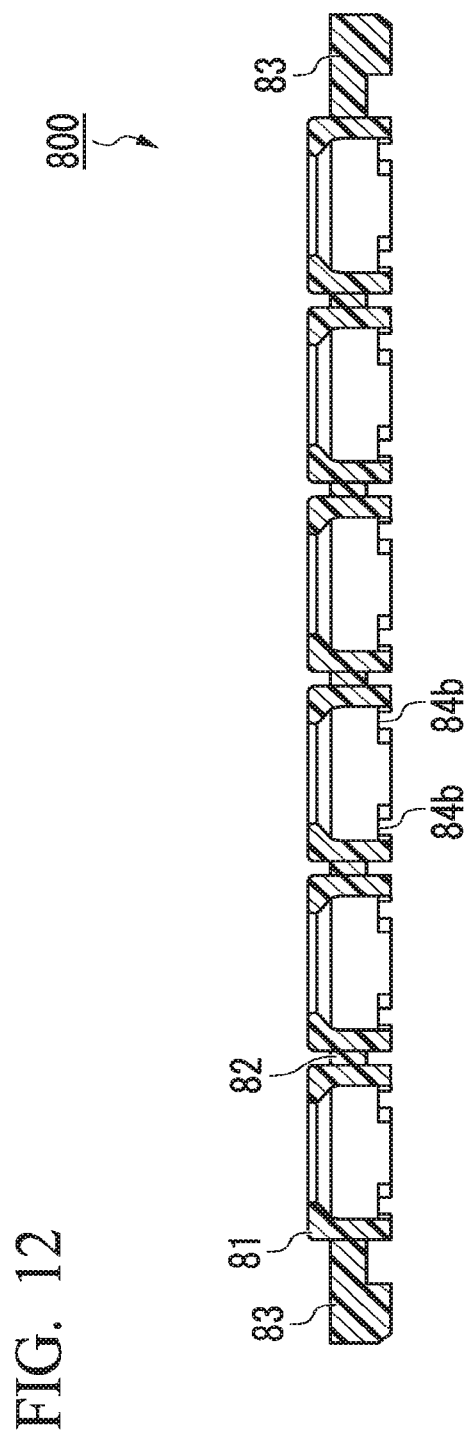
FIG. 12 is an enlarged sectional view in the direction of arrow line XII-XII' in FIG. 10.
Figure 13:
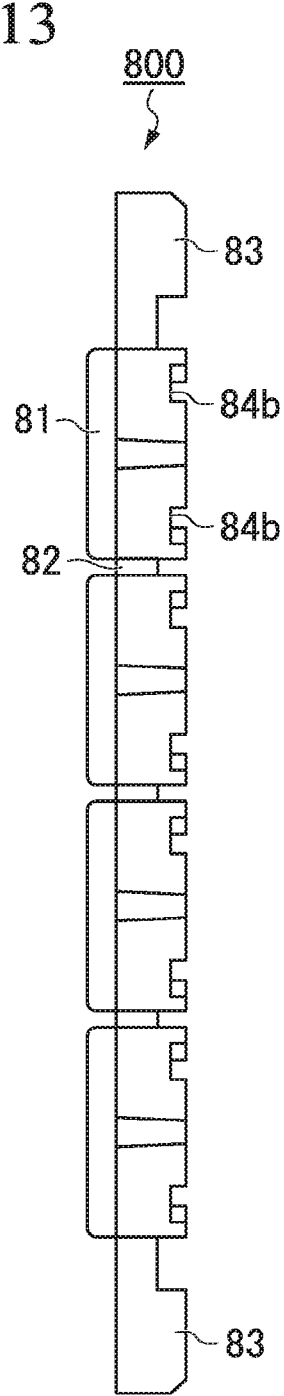
FIG. 13 is an enlarged side view of the liquid flow control body illustrated in FIG. 10.

FIG. 5 is a plan view of a cell aggregate culture vessel 6 of Embodiment 2. FIG. 6 is a sectional view in the direction of arrow line VI-VI' in FIG. 5. FIG. 7 is an enlarged end view cut in the direction of arrow line VII-VII' in FIG. 5. FIG. 8 is a plan view of a multi-well plate body 61 constituting the cell aggregate culture vessel 6 of Embodiment 2, and FIG. 9 is a sectional view in the direction of arrow line IX-IX' in FIG. 8. FIG. 10 is a plan view of a liquid flow control body 800 constituting the cell aggregate culture vessel 6 of Embodiment 2, FIG. 11 is a bottom surface view of the liquid flow control body 800 illustrated in FIG. 10, FIG. 12 is an enlarged sectional view in the direction of arrow line XII-XII' in FIG. 10, FIG. 13 is an enlarged side view of FIG. 10, and FIG. 14 is an enlarged perspective view of the liquid flow control body 800 illustrated in FIG. 11.

The culture vessel 6 of Embodiment 2 which will be described using FIGS. 5 to 14, similar to the culture vessel 1 of Embodiment 1, includes a plurality of wells 71 formed in a plate-like body 7, tubular bodies 81 disposed above the respective wells 71, a side wall 9 which protrudes above the openings of a plurality of the wells 71 and surrounds a plurality of the wells 71, and a base 10 which protrudes below the openings of a plurality of the wells 71. However, the culture vessel 6 of Embodiment 2 is different from the culture vessel 1 of Embodiment 1 because the tubular bodies 81 constitute the liquid flow control body 800 including a connected body 80 (refer to FIGS. 10 and 11) of a plurality of the tubular bodies 81 and communication portions 81b are slits in the circumferential directions of the tubular bodies 81.

Figure 11:
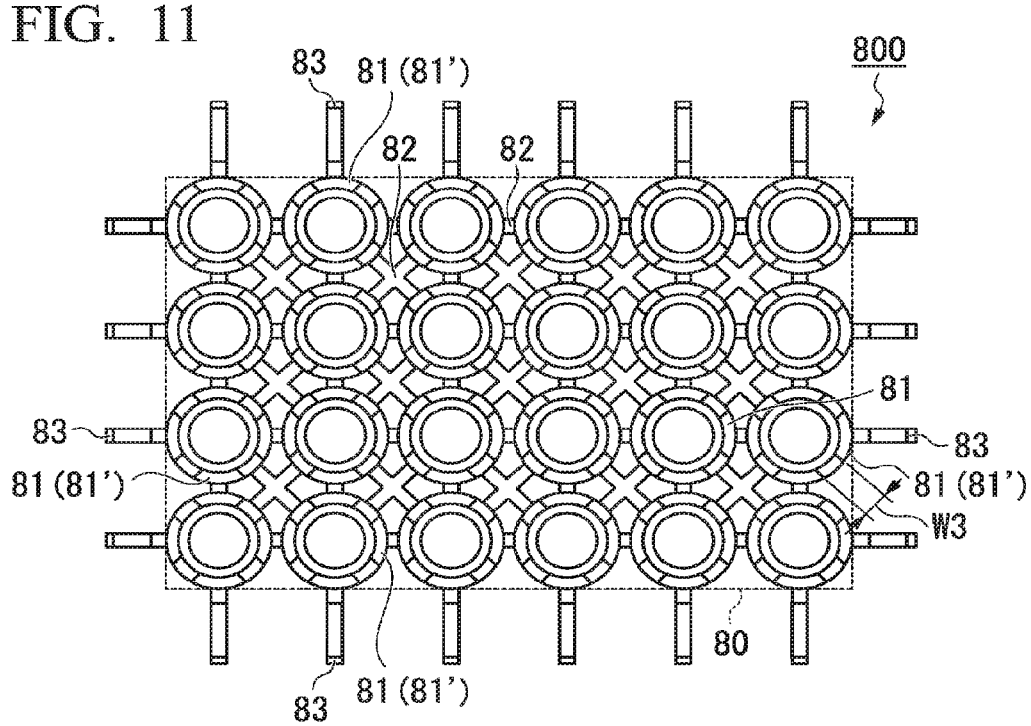
FIG. 11 is a bottom surface view of the liquid flow control body illustrated in FIG. 10.
Figure 14:
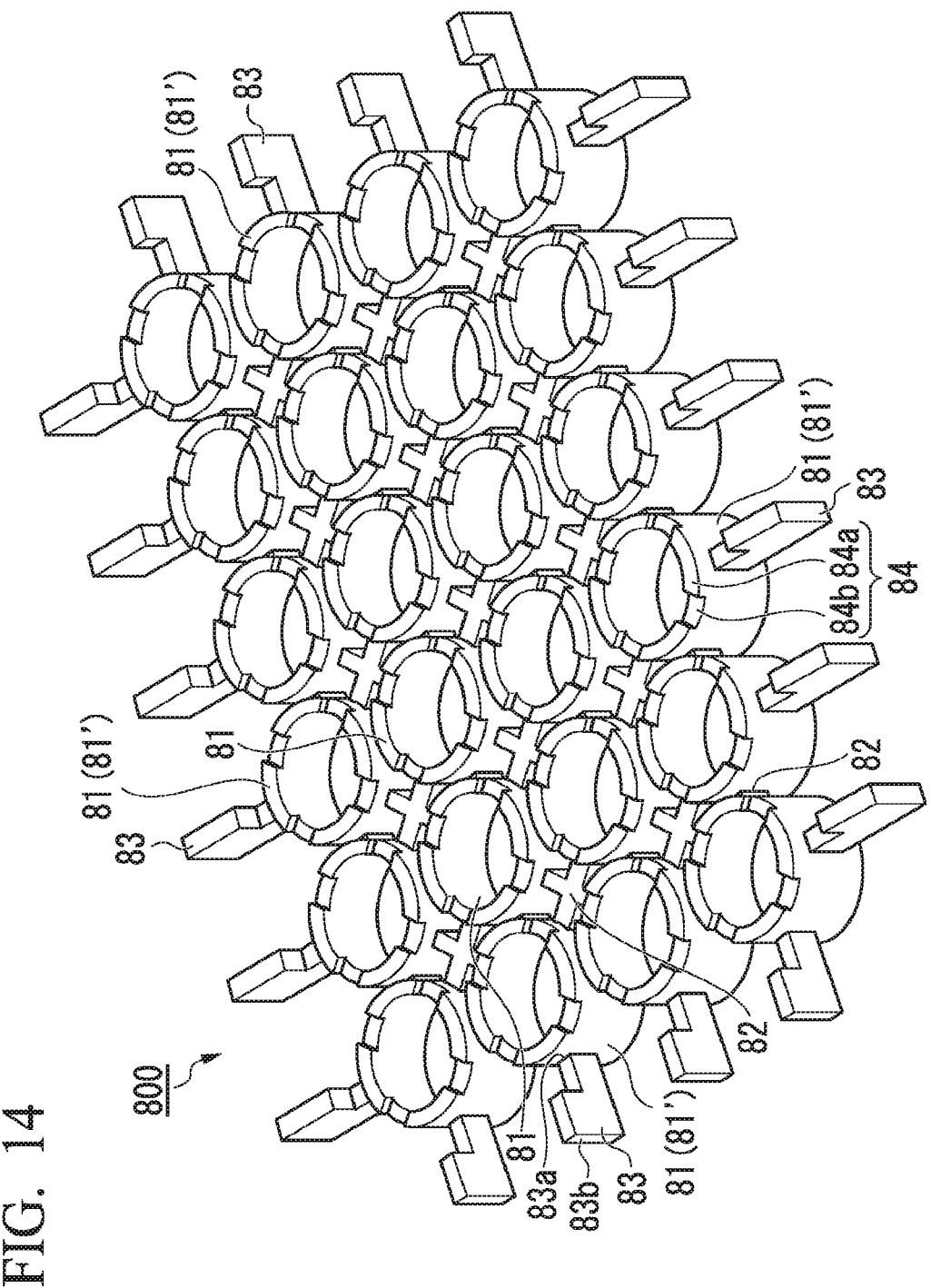
FIG. 14 is an enlarged perspective view of the liquid flow control body illustrated in FIG. 11.

The culture vessel 6 of Embodiment 2 includes the multi-well plate body 61 (refer to FIGS. 8 and 9) and the liquid flow control body 800 (refer to FIGS. 10, 11, and 14). The multi-well plate body 61 includes a plurality of the wells 71 formed in the plate-like body 7, the side wall 9 which protrudes above the openings of a plurality of the wells 71 and surrounds a plurality of the wells 71, and the base 10 which protrudes below the openings of a plurality of the wells 71. For convenience, a direction intersecting the plane of the plate-like body 7 at right angles will be referred to as the "vertical direction" (Z-axis direction), the tubular body 81 side will be referred to as being "above", and the well 71 side will be referred to as being "below". Furthermore, the central axes 81a (refer to FIG. 7) of the tubular bodies 81 are parallel to the vertical direction and the Z-axis direction and coincide with the central axes of the wells 71.

In the culture vessel 6 of Embodiment 2, the liquid flow control body 800 may not be joined to the multi-well plate body 61 and may be a separate body from the multi-well plate body 61 or may be integrated with the multi-well plate body 61 by means of joining.

As clearly observed from FIG. 14, on an end surface (bottom surface) 84 on the well 71 side of each of the tubular bodies 81 constituting the liquid flow control body 800, at least one groove 84b is formed, a plurality of grooves 84b are preferably formed in the circumferential direction, and a plurality of grooves 84b are more preferably formed in the circumferential direction at equal intervals. As is clear from FIG. 7, in a state in which the liquid flow control body 800 is disposed on one surface 7a of the plate-like body 7, the grooves 84b constitute communication portions 81b which can discharge culture fluids without allowing the passage of cell aggregates to the outside of the tubular bodies 81, and in end surfaces (bottom surfaces) 84 on the well 71 side of the respective tubular bodies 81, portions 84a in which the grooves 84b are not formed are in contact with one surfaces 7a of the plate-like plate 7 respectively. That is, in a state in which the liquid flow control body 800 is disposed on one surface 7a of the plate-like body 7, the grooves 84b are formed in the tubular bodies 81 and constitute slits 81b which are along the circumferential directions of the tubular bodies 81.

In an example of the culture vessel 6 of Embodiment 2 which will be described using FIGS. 5 to 14, the communication portions (the slits along the circumferential directions of the tubular bodies 81) capable of discharging culture fluids in the wells 71 to the outside of the tubular bodies 81 are slits formed by surfaces constituting the grooves 84b in the end surfaces (bottom surfaces) 84 on the well 71 side of the tubular bodies 81 and portions in one surface 7a of the plate-like body 7 which face the grooves 84b, but the slits along the circumferential directions of the tubular bodies 81 are not limited thereto. The slits along the circumferential directions of the tubular bodies 81 may be, for example, through-holes which penetrate the tubular walls of the tubular bodies 81 in the thickness direction thereof and have the longitudinal direction along the circumferential directions of the tubular bodies 81 as long as, when the culture vessel 1 is inclined in order to discharge some of the culture fluids, some of the culture fluids in the wells 71 can be appropriately discharged without allowing cell aggregates to exit from the wells 71. Alternatively, the longitudinal directions of the slits may be parallel to the central axes 81a (refer to FIG. 7) of the tubular bodies 81.

The depth of the groove 84b or the width W2 of the slit (refer to FIG. 7) needs to be smaller than the diameter of a cell aggregate, which is soon to be moved to the culture vessel 6 of Embodiment 2, measured by means of microscopic observation, and, in a case in which the diameter of the cell aggregate is in a range of 600 µm to 700 µm, the depth or width is preferably 0.1 mm or larger, more preferably 0.2 mm or larger, and still more preferably 0.25 mm or larger from the viewpoint of improvement in the discharge efficiency of culture fluids, and the depth or width is preferably 0.5 mm or smaller, more preferably 0.4 mm or smaller, and still more preferably 0.3 mm or smaller from the viewpoint of reducing the possibility of cell aggregates flowing out.

The length W3 in the circumferential direction of the groove 84b or the slit (refer to FIG. 11) is preferably 2 mm or larger from the viewpoint of improvement in the discharge efficiency of culture fluids.

In an example of the culture vessel 6 of Embodiment 2 which will be described using FIGS. 5 to 14, the number of the communication portions 81b is four, but there is no particular limitation regarding the number of the communication portions 81b. However, the number of the communication portions is preferably two or more and more preferably four or more since it is easy to efficiently discharge culture fluids from the wells 71 and the above-described fresh culture fluids are allowed to easily and uniformly move into the respective wells 71. In addition, in a case in which the culture vessel 6 of Embodiment 2 includes two or more communication portions 81b, a pair of the communication portions 81b selected from the two or more communication portions 81b are preferably separated from each other in the circumferential direction at 90 degrees or more.

In an example of the culture vessel 6 of Embodiment 2 which will be described using FIGS. 5 to 14, the shape of the inner surface of the well 71 is a hemispherical shape; however, in the culture vessel 6 of Embodiment 2, the form of the well 71 is not limited thereto and may be the same form as that of the culture vessels 1 of Embodiment 1. The diameter of the well 71 at the opening, the depth of the well 71, the capacity per inside space in a structure made up of the wells 71 and the tubular bodies 81, the capacity of each of the wells 71, and the like are also the same as those in the culture vessels 1 of Embodiment 1.

As is clear from FIGS. 10 and 11, the liquid flow control body 800 includes the connected body 80 which is a plurality of the tubular bodies 81 connected together through crosslinking portions 82 and a position-regulating portion 83. In the liquid flow control body 800, a plurality of the tubular bodies 81 are connected to each other through the crosslinking portions 82 disposed between adjacent tubular bodies 81. As illustrated in FIG. 7 and the like, the crosslinking portions 82 are respectively connected to the tubular bodies 81 at the central portions of the outer circumferential surfaces of the tubular bodies 81 in the vertical direction so that faces 82a of the crosslinking portions which face the plate-like plate 7 do not come into contact with the one surface 7a of the plate-like body 7, and thus there are voids C1 between the crosslinking portions 82 and the one surface 7a of the plate-like body 7. In addition, as is clear from FIGS. 10 and 11, the position-regulating portions 83 are respectively connected to, out of a plurality of the tubular bodies 81, tubular bodies 81' disposed at the outer edge of the connected body 80.

As illustrated in FIG. 6, one end 83a of the position-regulating portion 83 is connected to the tubular body 81 at a central portion of the outer circumferential surface of the tubular body 81 in the vertical direction, and the end surface at the other end 83b of the position-regulating portion 83 is in contact with an inner surface 9a of the side wall 9. Therefore, for example, in a case in which the liquid flow control body 800 is a separate body from the multi-well plate body 61, movement of the liquid flow control body 800 disposed on one surface 7a of the plate-like body 7 in a direction parallel to an X axis and a direction parallel to a Y axis is prevented (refer to FIG. 5), and the respective tubular bodies 81 are guaranteed being disposed at predetermined positions above the corresponding wells 71 at all times, and, in a case in which the liquid flow control body 800 is joined to the multi-well plate body 61, it becomes easy to determine the position of the liquid flow control body 800 during joining.

As illustrated in FIG. 6, in the surfaces of the position-regulating portions 83 which face the plate-like body 7, at least portions 83c which are closer to the tubular bodies 81 are connected to the tubular bodies 81 at the central portions of the outer circumferential surfaces of the tubular bodies 81 in the vertical direction so as not to come into contact with one surface 7a of the plate-like body 7, and thus there are voids C2 between the position-regulating portions 83 and one surface 7a of the plate-like body 7. Therefore, culture fluids discharged from the wells 71 through the communication portions (the slits) 81b by inclining the culture vessel 6 can be collected into, for example, the corners of the culture vessel through the voids C1 and the voids C2.

On the other hand, the end portions (the other end portions) of the position-regulating portions 83 which are away from the tubular bodies 81 are preferably in contact not only with the inner surface 9a of the side wall 9 but also with one surface 7a of the plate-like body 7 since it is easy to determine the position of the liquid flow control body 800 in the multi-well plate body 61.

In the culture vessel 6 of Embodiment 2 described using FIGS. 5 to 14, the position-regulating portions 83 are connected to, out of a plurality of the tubular bodies 81, all of the tubular bodies 81' disposed at the outer edge of the connected body 80. However, the culture vessel 6 of Embodiment 2 is not limited thereto. The liquid flow control body 800 may include at least a pair of the position-regulating portions 83 having one end portion connected to the connected body 80 and the other end portion in contact with the inner surface of the side wall 9, one of the position-regulating portions 83 may come into contact with one of the inner surfaces 9a of the side wall 9 which face each other, and the other of the position-regulating portions 83 may come into contact with the other of the inner surfaces 9a of the side wall 9 which face each other. In such a case, in a case in which the liquid flow control body 800 is joined to the multi-well plate body 61, it is possible to easily determine the position of the liquid flow control body 800 on one surface 7a of the plate-like body 7 during joining. In addition, in a case in which the liquid flow control body 800 is a separate body from the multi-well plate body 61, it is possible to suppress the liquid flow control body 800 moving on one surface 7a of the plate-like body 7.

From the same viewpoint, it is preferable that the liquid flow control body 800 includes two pairs of the position-regulating portions 83, as illustrated in FIG. 5, one position-regulating portion of a pair of the position-regulating portions 83' comes into contact with one of the inner surfaces of the side wall 9 which face each other in the Y-axis direction, the other position-regulating portion 83' comes into contact with the other of the inner surfaces of the side wall 9 which face each other in the Y-axis direction, one position-regulating portion 83" of a pair of position-regulating portions 83" comes into contact with one of the inner surfaces of the side wall 9 which face each other in the X-axis direction, and the other position-regulating portion 83" comes into contact with the other of the inner surfaces of the side wall 9 which face each other in the X-axis direction.

Materials for the culture vessel 6 of Embodiment 2 may be the same as those for the culture vessel 1 of Embodiment 1. The culture vessel 6 of Embodiment 2 can be manufactured by separately molding the multi-well plate body 61 and the liquid flow control body 800 respectively, and, for example, joining these components or disposing the liquid flow control body 800 in the multi-well plate body 6.

When the culture vessel 6 of Embodiment 2 is used in the above-described "cell aggregate culture method", there is little influence on cell aggregates, and culture fluids can be efficiently exchanged with each other, and thus cell aggregates can be efficiently cultured.

Embodiment 3

Figure 15A:
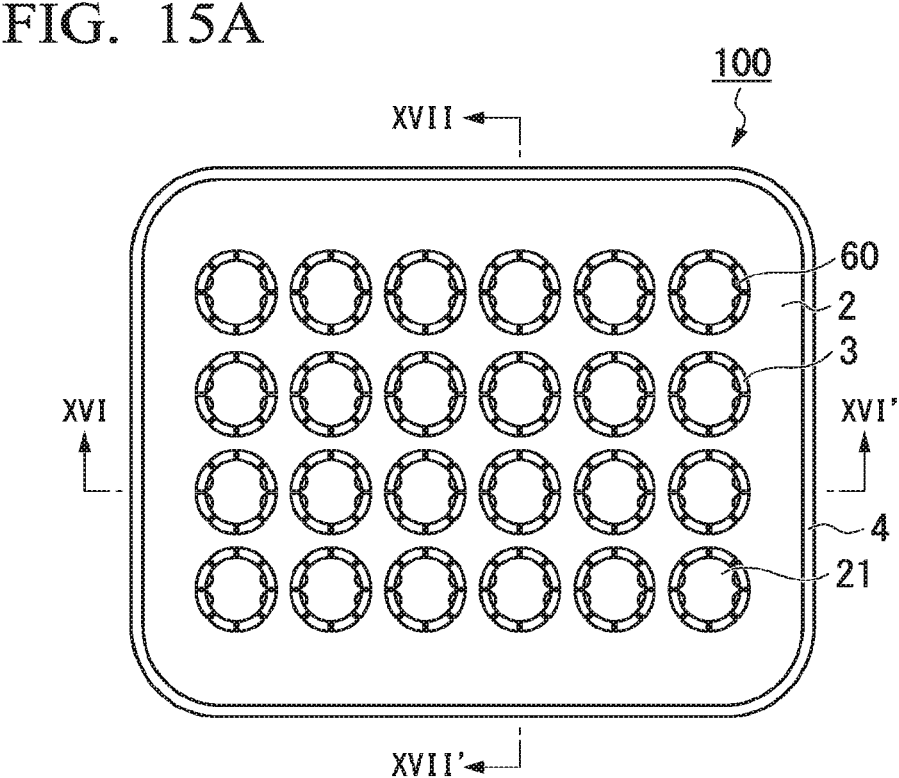
FIG. 15A is a plan view of a cell aggregate culture vessel of Embodiment 3.
Figure 15B:
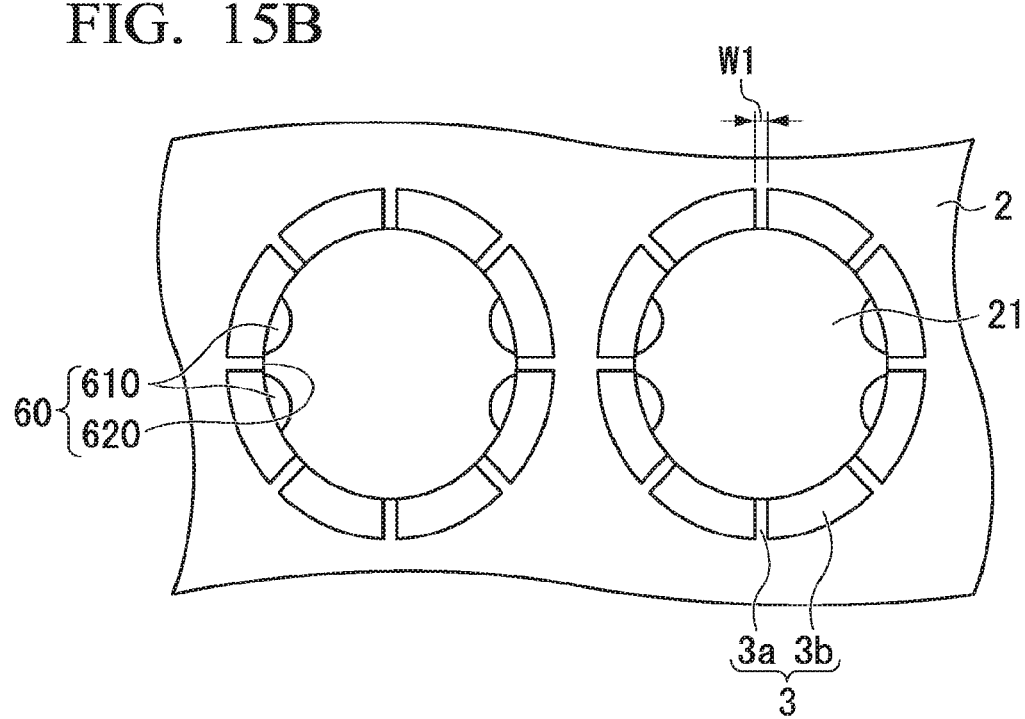
FIG. 15B is a partial enlarged view of FIG. 15A.
Figure 16:
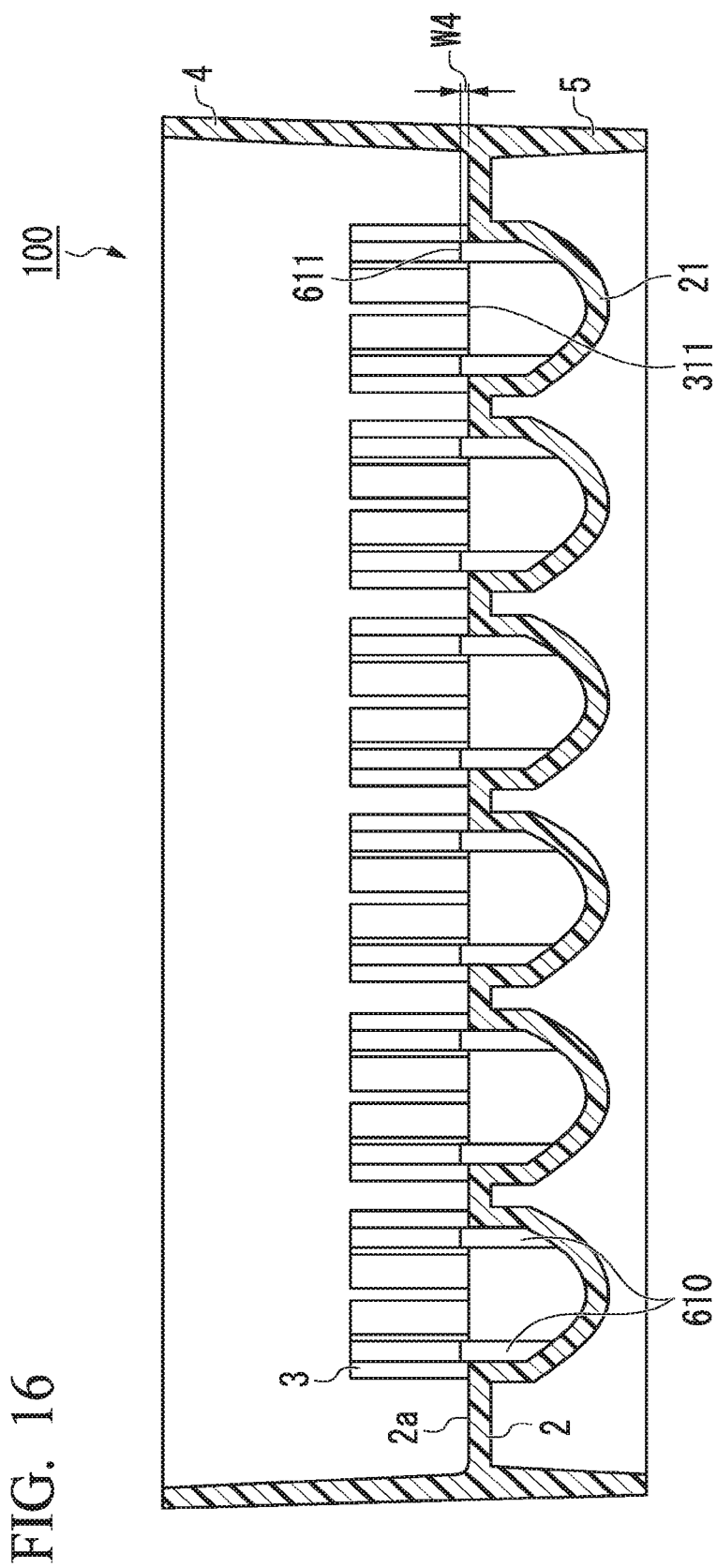
FIG. 16 is an enlarged sectional view in the direction of arrow line XVI-XVI' in FIG. 15A.
Figure 17A:
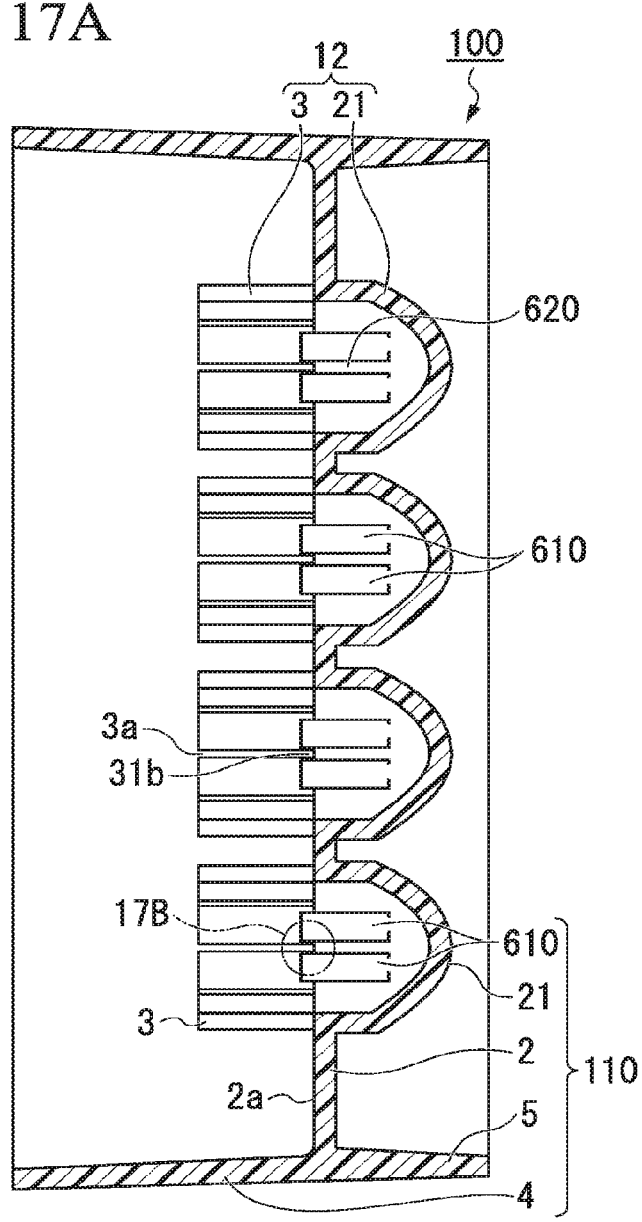
FIG. 17A is an enlarged sectional view in the direction of arrow line XVII-XVII' in FIG. 15A.
Figure 17B:
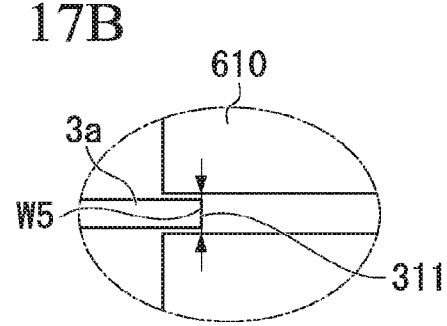
FIG. 17B is a partial enlarged view of FIG. 17A.
Figure 18:
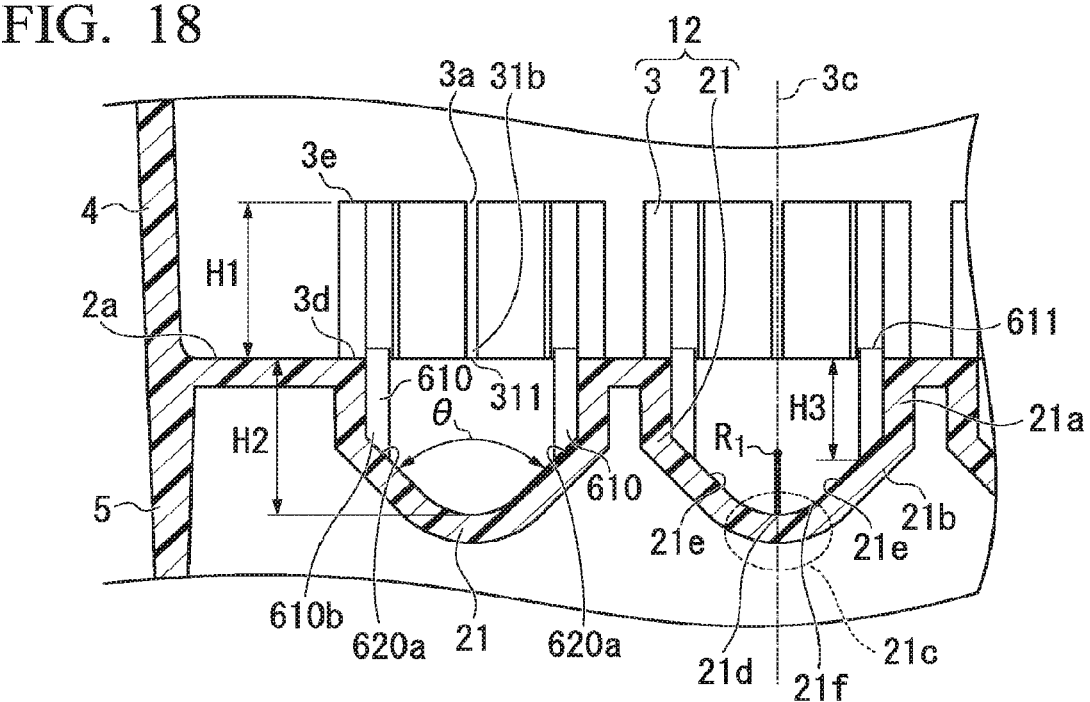
FIG. 18 is a partial enlarged view of FIG. 16.
Figure 19:
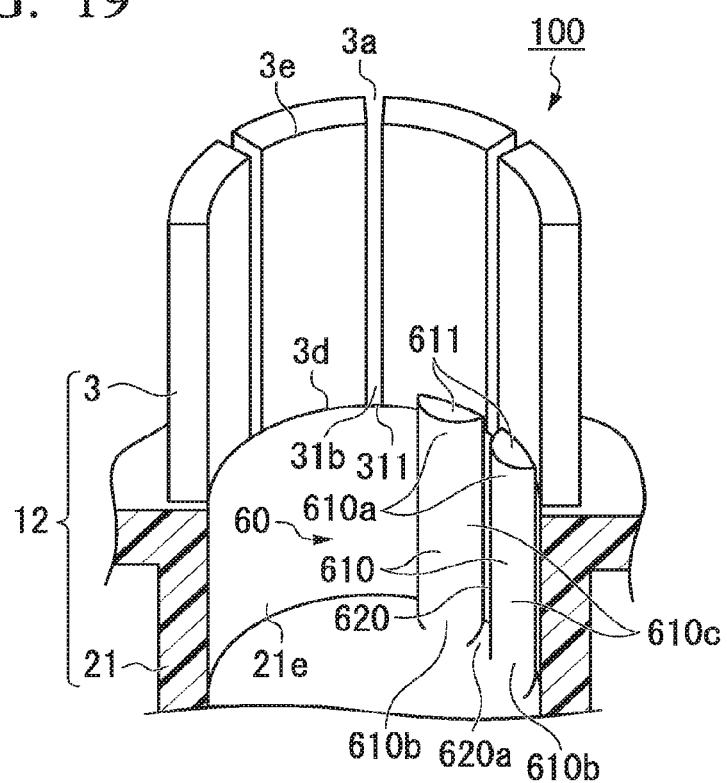
FIG. 19 is a perspective sectional view for describing an internal structure of a structure made up of a tubular body and a well of the cell aggregate culture vessel illustrated in FIG. 15A.
Figure 20:
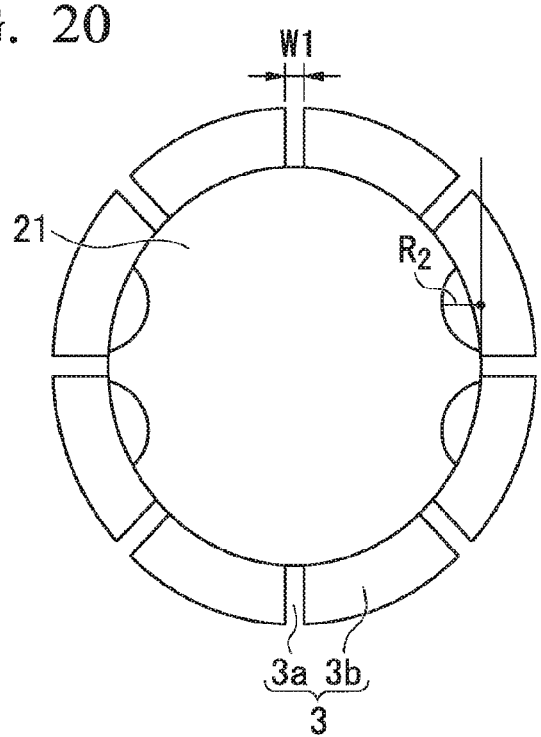
FIG. 20 is a partial enlarged view of FIG. 15A.
Figure 21:
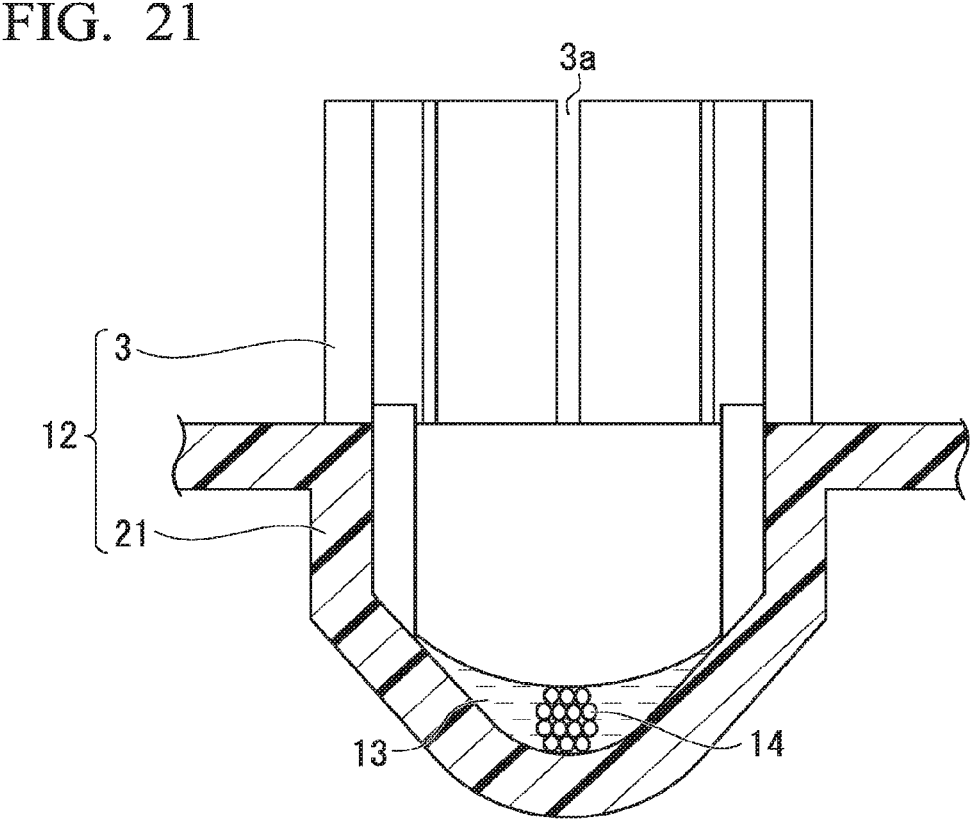
FIG. 21 is a conceptual view for describing a state after a cell aggregate is cultured in a culture fluid for a predetermined time using the cell aggregate culture vessel illustrated in FIG. 15A and then some of the culture fluid in the well is discharged.

FIG. 15A is a plan view of a cell aggregate culture vessel 100 of Embodiment 3, FIG. 15B is a partial enlarged view of FIG. 15A. FIG. 16 is an enlarged sectional view in the direction of arrow line XVI-XVI' in FIG. 15A. FIG. 17A is a sectional view in the direction of arrow line XVII-XVII' in FIG. 15A, and FIG. 17B is a partial enlarged view of FIG. 17A. FIG. 18 is a partial enlarged view of FIG. 16, and FIG. 19 is a perspective sectional view for describing an internal structure of the structure 12 made up of the tubular body 3 and the well 21 of the cell aggregate culture vessel 100. FIG. 20 is a partial enlarged view of FIG. 15A, and FIG. 21 is a conceptual view for describing a state after a cell aggregate 14 is cultured in a culture fluid 13 for a predetermined time using the cell aggregate culture vessel 100 of the present disclosure and then some of the culture fluid 13 in the well 21 is discharged to the outside of the structure 12 through the communication portion 3a.

The culture vessel 100 of Embodiment 3 which will be described using FIGS. 15A to 21 is a vessel for culturing cell aggregates and has the same constitution as those of the above-described cell aggregate culture vessels of Embodiment 1 and Embodiment 2 except for the fact that liquid guide portions described below are provided. Specifically, the culture vessel 100 includes a plurality of the wells 21 formed in the plate-like body 2 and the tubular bodies 3 disposed above the respective wells 21. For convenience, a direction intersecting the plane of the plate-like body 2 at right angles will be referred to as the "vertical direction", the tubular body 3 side will be referred to as being "above", and the well 21 side will be referred to as being "below".

The culture vessel 100 of Embodiment 3 includes the side wall 4 which protrudes above the openings of a plurality of the wells 21 and surrounds a plurality of the wells 21 and the base 5 which protrudes below the openings of a plurality of the wells 21. The shapes of the outer surface and the inner surface of the side wall 4 when the culture vessel 100 is seen in plan view are substantially rectangular respectively. The base 5 protrudes further than the wells 21 from the plate-like body 2, and thus, when the culture vessel 1 is placed on a horizontal surface, the end surface of the base 5 comes into contact with the horizontal surface.

The respective wells 21 have a culture space capable of storing cell aggregates and culture fluids. The tubular body 3 has a substantially cylindrical shape and has an inner cavity communicating with the culture space. In the tubular wall 3b of the tubular body 3, a plurality of the communication portions 3a are formed at equal intervals along the circumferential direction of the tubular body 3. The communication portion 3a is a slit which is parallel to the central axis 3c (refer to FIG. 18) of the tubular body 3 and is formed from the base end 3d to the front end 3e of the tubular body 3. Furthermore, the central axis 3c of the tubular body 3 is parallel to the vertical direction and coincides with the central axes of the wells 21 and the structure 12 (refer to FIGS. 17A, 17B, 18, 19, 21, and the like) made up of the tubular bodies 3 and the wells 21.

In an example of the culture vessel 100 of Embodiment 3 which will be described using FIGS. 15A to 21, one end (a lower side end 311, refer to FIGS. 18 and 19) of both ends of the slit 3a in the longitudinal direction which is closer to the well 21 coincides with the base end 3d of the tubular body 3, and the other end further from the well 21 coincides with the front end 3e of the tubular body 3. However, slits are not limited to the above-described example as long as, when the culture vessel 100 is inclined in order to discharge some of the culture fluids, some of the culture fluids in the wells 21 can be appropriately discharged without allowing cell aggregates to exit from the wells 21, and, when the culture vessel 100 is placed on a horizontal surface and fresh culture fluids are supplied, fresh culture fluids supplied to the outside of the structure 12 can be appropriately caused to flow into the wells 21. For example, slits may be formed toward the front ends 3e of the tubular bodies 3 from above the base ends 3d of the tubular bodies 3.

In an example of the culture vessel 100 of Embodiment 3 which will be described using FIGS. 15A to 21, the number of the communication portions 3a (slits) is eight, but there is no particular limitation regarding the number of the communication portions 3a. However, the number of the communication portions is preferably two or more, more preferably four or more, and still more preferably six or more since the properties of culture fluids being discharged from the respective wells 21 are improved, and fresh culture fluids described below are allowed to easily and uniformly move into the respective wells. In addition, in a case in which each of the wells 21 includes two or more communication portions 3a, the angle between a pair of the communication portions 3a selected from the two or more communication portions 3a which are separated from each other in the circumferential direction is preferably 90 degrees or more and more preferably 180 degrees or more since culture fluids are efficiently discharged.

In one or a plurality of embodiments, as illustrated in FIG. 15B, the width W1 (the width in the circumferential direction) of the slit needs to be smaller than the diameter of a cell aggregate, which is soon to be moved to the culture vessel, measured by means of microscopic observation, and, in a case in which the diameter of the cell aggregate is in a range of 600 μm to 700 μm, the width is preferably 0.1 mm or larger, more preferably 0.2 mm or larger, and still more preferably 0.25 mm or larger from the viewpoint of improvement in the properties of culture fluids being discharged and the properties of fresh culture fluids flowing into the wells, and the width is preferably 0.5 mm or smaller, more preferably 0.4 mm or smaller, and still more preferably 0.3 mm or smaller from the viewpoint of reducing the possibility of cell aggregates flowing out.

In a cell aggregate culture method of the present disclosure described below, the liquid surface of culture fluids is preferably placed above the base ends 3d (the lower side ends 311 of the communication portions 3a) of the tubular bodies 3 in order for the quality of culture fluids in a plurality of the wells 21 to be made uniform by means of diffusion using the communication portions 3a. In the culture method, the height H1 (refer to FIG. 18) of the tubular body 3 is preferably in a range of 1 mm to 7 mm and more preferably in a range of 3 mm to 5 mm so as to prevent cell aggregates from floating on culture fluids, exceeding the front end of the tubular body 3, and moving into a space between the tubular body 3 and an adjacent tubular body 3, adjacent tubular bodies 3, and adjacent wells 21.

In one or a plurality of embodiments, the openings of a plurality of the wells 21 are in the same plane as one surface 2a (refer to FIGS. 16 to 18) of the plate-like body 2 connecting a plurality of the wells 21 together, and the tubular bodies 3 are disposed on the surface 2a, but the slits which are the communication portion 3a are preferably formed from the base ends 3d (refer to FIGS. 18 and 19) of the tubular bodies 3 from the viewpoint of improvement in the properties of culture fluids being discharged.

In order to suppress physical stimuli from being applied to cell aggregates in the middle of the discharging of culture fluids, in one or a plurality of embodiments, it is preferable that there are no levels on the inner surface (however, portions in which liquid guide portions 60 described below are formed are excluded) of the structure 12 (refer to FIGS. 17A, 17B, and 18) made up of the tubular bodies 3 and the wells 21, and specifically, it is preferable that the central axes 3c of the tubular bodies 3 coincide with the central axes of the wells 21 and the radii of cylindrical surfaces which are the inner circumferential surfaces of the tubular bodies 3 are equal to the radii of the openings of the wells 21. In addition, in a case in which, for example, the well 21 includes a tubular trunk portion 21a (refer to FIG. 18) and the inner surface of the trunk portion 21a is a cylindrical surface, it is preferable that the central axes 3c of the tubular bodies 3 coincide with the central axes of the wells 21 and the radii of the cylindrical surfaces which are the inner circumferential surfaces of the tubular bodies 3 are equal to the radii of the cylindrical surfaces which are the inner circumferential surfaces of the trunk portions 21a.

As illustrated in FIG. 18, each of the wells 21 includes the tubular trunk portion 21a and the funnel-shaped bottom portion 21b provided at one end of the trunk portion 21a. In the bottom portion 21b, the culture space in the well 21 contracts toward the front end (opposite to the opening) of the well 21. In the inner surface facing the culture space in the well 21, the central portion 21c of the bottom portion 21b is a curved surface. That is, the inner surface of the bottom portion 21b can be an inverted conic surface having a curved surface at the top portion. The trunk portion 21a may have, for example, a substantially cylindrical shape. In one or a plurality of embodiments of each of the wells 21, in a sectional view (refer to FIG. 18) of the well 21 cut on a plane including the central axis thereof, the inner surface of the bottom portion 21b has a substantially V shape and is arcuate in the central portion 21c. In one or a plurality of embodiments of each of the wells 21, the continuous portion between the trunk portion 21a and the bottom portion 21b in the inner surface is preferably a curved surface.

In addition, in one or a plurality of embodiments, in a case in which the well 21 is cut on a plane including the central axis thereof and is seen in plan view, the inner surface of the well 21 is substantially parallel to the central axis of the well 21 in the trunk portion 21a, includes a pair of the inclined surfaces 21e inclining toward the central axis passing through the top point 21d (the deepest portion) of the inner surface of the well 21 from the lower end side of the inner surface of the trunk portion 21a in the funnel-shaped bottom portion 21b, and includes an arcuate surface 21f in the central portion 21c of the bottom portion 21b.

In one or a plurality of embodiments, as illustrated in FIG. 18, the aperture angle $\theta$ of the bottom portion 21b is preferably greater than 60 degrees and 100 degrees or smaller, more preferably in a range of 70 degrees to 100 degrees, and still more preferably in a range of 80 degrees to 90 degrees since it is possible to efficiently culture cell aggregates. The "aperture angle" in the present disclosure refers to the angle formed by the pair of inclined surfaces 21c and is, for example, the angle indicated by $\theta$ in FIG. 18.

In one or a plurality of embodiments, the curvature radius $R_1$ on the central portion inner surface of the bottom portion 21b is preferably in a range of 0.5 mm to 2.0 mm since, during the exchange of culture fluids, cell aggregates are not exposed on the surface of the culture fluids and stimuli being applied to cell aggregates can be suppressed and is more preferably in a range of 1.0 mm to 2.0 mm since it is easy to observe cell aggregates using an optical microscope. Furthermore, in the present specification, the "curvature radius of the central portion inner surface" refers to a radius corresponding to a circumference including a curved surface in which the curvature of the front end portion of the bottom portion 21b of the well 21 is $1/R_1$. The curvature radius $R_1$ of the central portion inner surface can be measured using laser distance meters or by means of actual measurements of cut sections of molded products.

In one or a plurality of embodiments, in a case in which the structure 12 (refer to FIG. 18) made up of the wells 21 and the tubular bodies 3 is cut on a plane including the central axis thereof and is seen in plan view, the length 112 (refer to FIG. 18) from one end (the lower side end 311) of both ends of the slit 3a in the longitudinal direction which is closer to the well 21 to the deepest portion 21d of the well 21 is preferably in a range of 3.0 mm to 6.0 mm since, after some of the culture fluids are removed in order to exchange culture fluids, cell aggregates to which new culture fluids are yet to be added are not exposed on the surface of culture fluids and damage or stimuli being applied to cell aggregates due to the removal of culture fluids are reduced and is more preferably in a range of 3.0 mm to 5.0 mm since, furthermore, a sufficient amount of nutrients and oxygen are supplied to cell aggregates.

In a case in which the slit 3a is formed toward the front end 3e of the tubular body 3 from the base end 3d of the tubular body 3, the depth of the well 21 is preferably in a range of 3.0 mm to 6.0 mm since, after some of the culture fluids are removed in order to exchange culture fluids, cell aggregates to which new culture fluids are yet to be added are not exposed on the surface of culture fluids and damage or stimuli being applied to cell aggregates due to the removal of culture fluids are reduced and is more preferably in a range of 3.0 mm to 5.0 mm since, furthermore, a sufficient amount of nutrients and oxygen are supplied to cell aggregates.

In one or a plurality of embodiments, the diameter of the well 21 at the opening is, for example, preferably 4.0 mm or larger since operability is excellent in a case in which multi dispensers are used and is preferably 11.0 mm or smaller since the number of the wells 21 per culture vessel increases.

In one or a plurality of embodiments, the capacity of the structure 12 (refer to FIG. 18) made up of the wells 21 and the tubular bodies 3 per inside space, in other words, the sum of the capacity of the culture spaces of the wells 21 (the inside spaces of the wells 21) and the capacity of the inside spaces in the inner circumferential surfaces (for example, cylindrical surfaces) of the tubular bodies 3 is not particularly limited, but is, for example, preferably in a range of 50 pt to 500 μL since a sufficient amount of culture fluids or reagents can be added in order to culture cell aggregates and is more preferably in a range of 50 μL to 200 μL since the amount of culture fluids or reagents being used decreases.

Furthermore, the form of the well in the culture vessel of the present embodiment is not limited to the well including the trunk portion 21a and the funnel-shaped bottom portion 21b. The form of the well may be, for example, a form in which the inner surface has a hemispherical shape or a form in which a trunk portion and a bottom portion are provided and the bottom portion has a hemispherical shape as long as it is possible to discharge some of the culture fluids in wells without allowing cell aggregates to exit from wells.

The culture vessel 100 includes the liquid guide portions 60 formed in the inner surface of the structure 12 made up of the tubular bodies 3 and the wells 21. As is clear from FIG. 19, the liquid guide portion 60 includes a liquid guide assisting groove 620 formed by a pair of protrusion portions 610 formed on the inner surface of the structure 12. The liquid guide assisting groove 620 is provided by forming a pair of the protrusion portions 610 on the inner surface of the structure 12 so that the upper side end surface 611 of each of the protrusion portions 61 is disposed above the lower side ends 311 of the slits 3a and forming the protrusion portions 610 along the same direction as the longitudinal direction of the respective slits 3a on both sides of at least one slit 3a in the width direction in the inner surface of the structure 12 made up of the tubular bodies 3 and the wells 21. In the culture vessel 100 in which the slits 3a are formed from the base ends 3d of the tubular bodies 3, the upper side end portion 610a of each of the protrusion portions 610 and the lower side end portions 31b of the slits 3a are disposed at the same positions in the vertical direction. When the liquid guide assisting grooves 620 are provided in the culture vessel 100, it is assumed that the properties of fresh culture fluids from the slits 3a flowing into the wells 21 and the properties of culture fluids in the wells 21 being discharged to the outside of the structure 12 are improved due to the capillary action. Furthermore, in the vertical direction, the side closer to the top point 21d (refer to FIG. 18) of the inner surface of the well 21 will be referred to as the "lower side" of the protrusion portion 610 and the "lower side" of the slit 3a, and the side further from the top point will be referred to as the "upper side" of the protrusion portion 610 and the "upper side" of the slit 3a.

As is clear from FIG. 18 and the like, lower side end portions 610b of the respective protrusion portions 610 reach the bottom surface (the inner surface of the bottom portion 21b of the well 21) in the inner surface of the well 21. One terminating end 620a of the liquid guide assisting groove 620 formed between a pair of the protrusion portions 610 is a closed end and is regulated by the inner surface of the bottom portion 21b of the well 21. The inner surface of the bottom portion 21b of the well 21 defining the terminating end 620a is a part of the inclined surface 21e (refer to FIG. 18) inclining downwards from the upstream side to the downstream side of the flow of culture fluids capable of flowing into the culture space in the well 21 from the slit 3a. The liquid guide assisting grooves 620 accelerate culture fluids to be discharged to the outside of the structure 12 through the slits 3a and to flow into the structure 12.

In one or a plurality of embodiments, the length W4 (refer to FIG. 16) in the vertical direction from the upper side end surface 611 of the protrusion portion 610 to a lower side end 311 of the slit 3a is preferably 0.1 mm or larger and more preferably 0.3 mm or larger since it is easy to improve the properties of fresh culture fluids from the slits 3a flowing into the wells 21. In one or a plurality of embodiments, there is no particular limitation regarding the upper limit of the length W4, and the protrusion portions 610 may be formed so as to reach the upper ends of the tubular bodies 3. Furthermore, in the culture vessel 100 illustrated in FIGS. 15A to 21, the slits 3a are formed from the base ends 3d (refer to FIGS. 18 and 19) to the front ends 3e of the tubular bodies 3, and thus W4 is equal to the lengths in the vertical direction of the portions formed on the inner surfaces of the tubular bodies 3 in the protrusion portions 610. However, in the present disclosure, the slits 3a are not necessarily formed from the base ends 3d of the tubular bodies 3, and, in a case in which the slits 3a are formed from above the base ends 3d of the tubular bodies 3, W4 is shorter than the lengths in the vertical direction of the portions formed on the inner surfaces of the tubular bodies 3 in the protrusion portions 610.

Furthermore, in the culture vessel 100 described using FIGS. 15A to 21, the upper side end surfaces 611 of the protrusion portions 610 are planes parallel to a plane intersecting the central axes 3c (refer to FIG. 18) of the tubular bodies 3 at right angles, and the lower side ends of the slits 3a are also regulated by a plane parallel to a plane intersecting the central axes 3c (refer to FIG. 18) of the tubular bodies 3 at right angles, the length W4 is constant along the circumferential direction of the tubular body. However, for example, since the upper side end surfaces 611 of the protrusion portions 610 are curved surfaces, in a case in which the length W4 is not constant along the circumferential direction of the tubular body, the length W4 is defined as the maximum length of lengths from the upper side end surfaces 611 of the respective protrusion portions 610 to the lower side ends of the slits 3a.

In one or a plurality of embodiments, the distance W5 (refer to FIG. 17B) between the protrusion portions 610 on the circumference passing through the lower side ends 311 of the slits 3a is preferably 0.3 mm or larger and more preferably 0.4 mm or larger and is preferably 1.0 mm or smaller and more preferably 0.7 mm or smaller since it is easy to improve the properties of fresh culture fluids from the slits 3a flowing into the wells 21 and the properties of culture fluids in the wells 21 being discharged to the outside of the structure 12, and it is possible to prevent cell aggregates from being sandwiched between a pair of the protrusion portions 610. Furthermore, the circumference passing through the lower side ends 311 of the slits 3a refers to a circumference having the center at a point which is on the central axis 3c (refer to FIG. 18) of the tubular body 3 and is on a plane including the lower side ends 311 of the slits 3a and intersecting the central axis 3c at right angles. In addition, W5 can be the distance between the protrusion portions 610 at the same position as that of the lower side end 311 of the slit 3a on the inner surface of the tubular body 3.

As is clear from FIG. 19, a surface 610c of each of the protrusion portions 610 which faces the culture space is a convex surface protruding toward the extended axis (the central axis of the well 21) of the central axis 3c of the tubular body 3. The convex surface is a curved surface which is higher in a portion further from the inner surface 21e (the inner surface of the trunk portion 21a) of the well 21 than in a portion close thereto. A section of the protrusion portion 610 in a case in which the protrusion portion 610 is cut in a direction intersecting the central axis 3c (refer to FIG. 18) of the tubular body 3 at right angles is, for example, an arch (a shape formed when a circle is divided into two parts using a single string) surrounded by an arc and a straight line. Alternately, the section has a shape regulated by an overlapping portion of two circles. When the surface 610c of each of the protrusion portions 610 which faces the culture space is the above-described convex surface, it is possible to reduce physical stimuli applied to cell aggregates from the respective protrusion portions 610.

In one or a plurality of embodiments, since it is easy to improve the properties of fresh culture fluids from the slits 3a flowing into the wells 21 and the properties of culture fluids in the wells 21 being discharged to the outside of the structure 12, and cell aggregates being sandwiched between a pair of the protrusion portions 610 are suppressed, it is preferable that the section of the protrusion portion has a shape regulated by an overlapping portion of two circles and the curvature radius $R_2$ (refer to FIG. 20) of the circumference which forms the arch or the shape regulated by an overlapping portion of two circles and includes an arc protruding toward the central axis of the tubular body is 0.5 mm or larger and 1.0 mm or smaller.

In one or a plurality of embodiments, since it is easy to improve the properties of fresh culture fluids from the slits 3a flowing into the wells 21 and the properties of culture fluids in the wells 21 being discharged to the outside of the structure 12, and cell aggregates being sandwiched between a pair of the protrusion portions 610 are suppressed, it is preferable that, as illustrated in FIG. 20, when the culture vessel 100 is seen in plan view, the center of a circle having the curvature radius $R_2$ as the radius passes through the center of the slit 3a in the width direction and is on a tangent line of a circumference including the inner surface of the tubular body 3.

In addition, in the culture vessel 100 of Embodiment 3 as well, similar to the culture vessel 1 of Embodiment 1, the cell adhesiveness reduction treatment is preferably carried out on the inner surface of at least the bottom portion 21b (refer to FIG. 18) of the well 21.

In the culture vessel 100 described using FIGS. 15A to 21, the numbers of the pairs of the protrusion portions 610 and the liquid guide assisting grooves 620 are respectively two in a single structure 12; however, in the culture vessel 100 of the present disclosure, the numbers of the pairs of the protrusion portions 610 and the liquid guide assisting grooves 620 are not limited thereto. The numbers of the pairs of the protrusion portions 610 and the liquid guide assisting grooves 620 provided may be one or more in consideration of the discharge amount of culture fluids in the wells 21 in accordance with the capacity of the wells 21 and the amount of culture fluids flowing into the wells 21.

In the culture vessel 100, the communication portions 3a capable of discharging culture fluids in the wells 21 to the outside of the tubular bodies 3 are slits which are formed in the tubular walls 3b of the tubular bodies 3 and are parallel to the central axes 3c (refer to FIG. 18) of the tubular bodies 3, but the communication portions 3a are not limited thereto. For example, the communication portions may be slits which penetrate the tubular walls 3b of the tubular bodies 3 in the thickness directions and have the longitudinal directions along the circumferential directions of the tubular bodies 3. Alternatively, the communication portions 3a are not limited to slits and may be, for example, through-holes which penetrate the tubular walls 3b of the tubular bodies 3 in the thickness directions.

In the culture vessel 100, the shape of the inner surface of the well 21 is a shape including the trunk portion 21a and the bottom portion 21b; however, in the culture vessel 10 of Embodiment 2, the form of the well 21 is not limited thereto and may be a hemispherical shape.

The culture vessel 100 of Embodiment 3 described using FIGS. 15A to 21 can be manufactured using the same method as for the culture vessel 1 of Embodiment 1. A multi-well plate body 110 (refer to FIG. 17A) including the plate-like body 2, a plurality of the wells 21 formed in the plate-like body 2, the protrusion portions 610, the side wall 4, and the base 5 can be molded in the same mold using an injection molding method.

The cell aggregate culture vessel of the present embodiment, similar to the cell aggregate culture vessel of Embodiment 2, may be constituted of a multi-well plate body and a liquid flow control body. In this case, the cell aggregate culture vessel, similar to the cell aggregate culture vessel of Embodiment 2, can be manufactured by separately molding the multi-well plate body and the liquid flow control body respectively, and, for example, joining these components or disposing the liquid flow control body in the multi-well plate body.

When the culture vessel 100 of Embodiment 3 is used in the above-described "cell aggregate culture method", there is little influence on cell aggregates, and culture fluids can be efficiently exchanged with each other, and thus cell aggregates can be efficiently cultured.

Embodiment 4

Figure 22A:
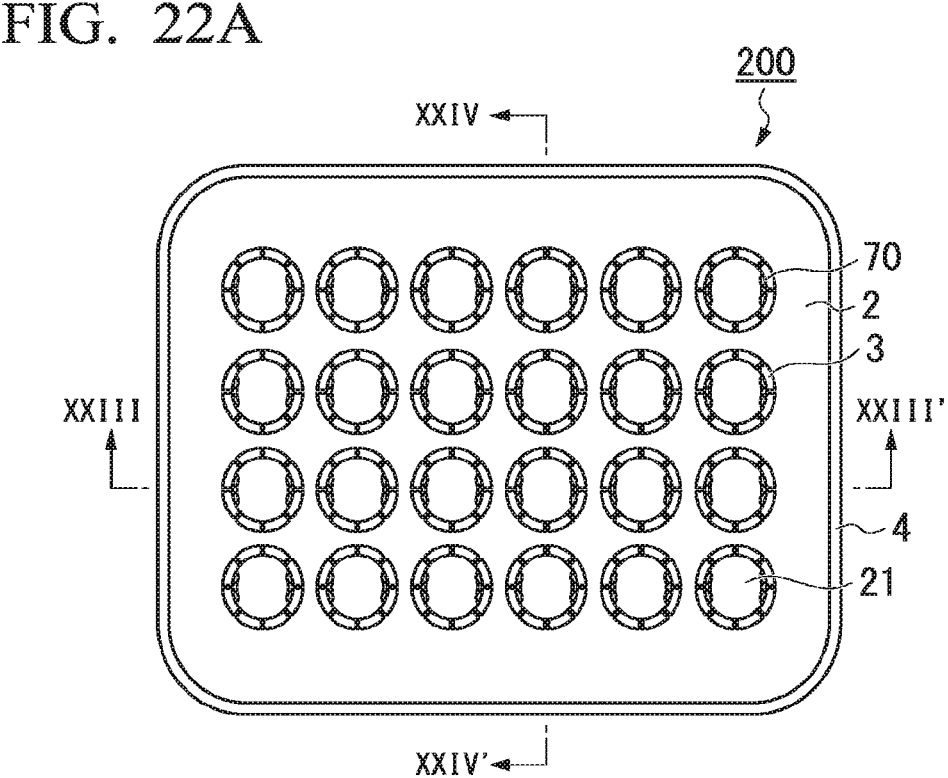
FIG. 22A is a plan view of a cell aggregate culture vessel of Embodiment 4.
Figure 22B:
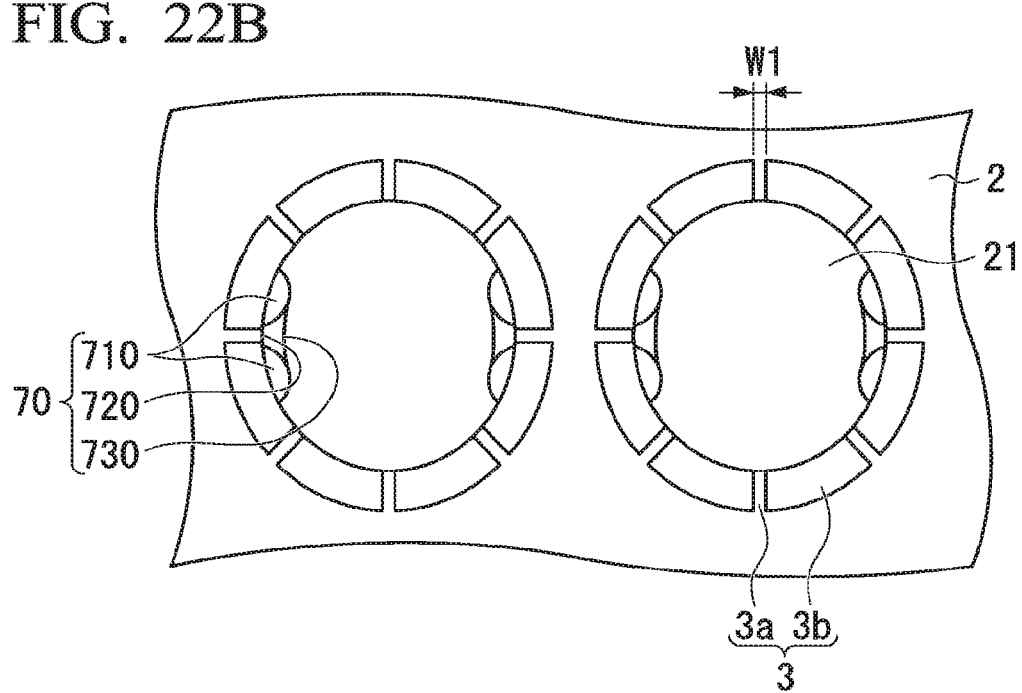
FIG. 22B is a partial enlarged view of FIG. 22A.
Figure 23:
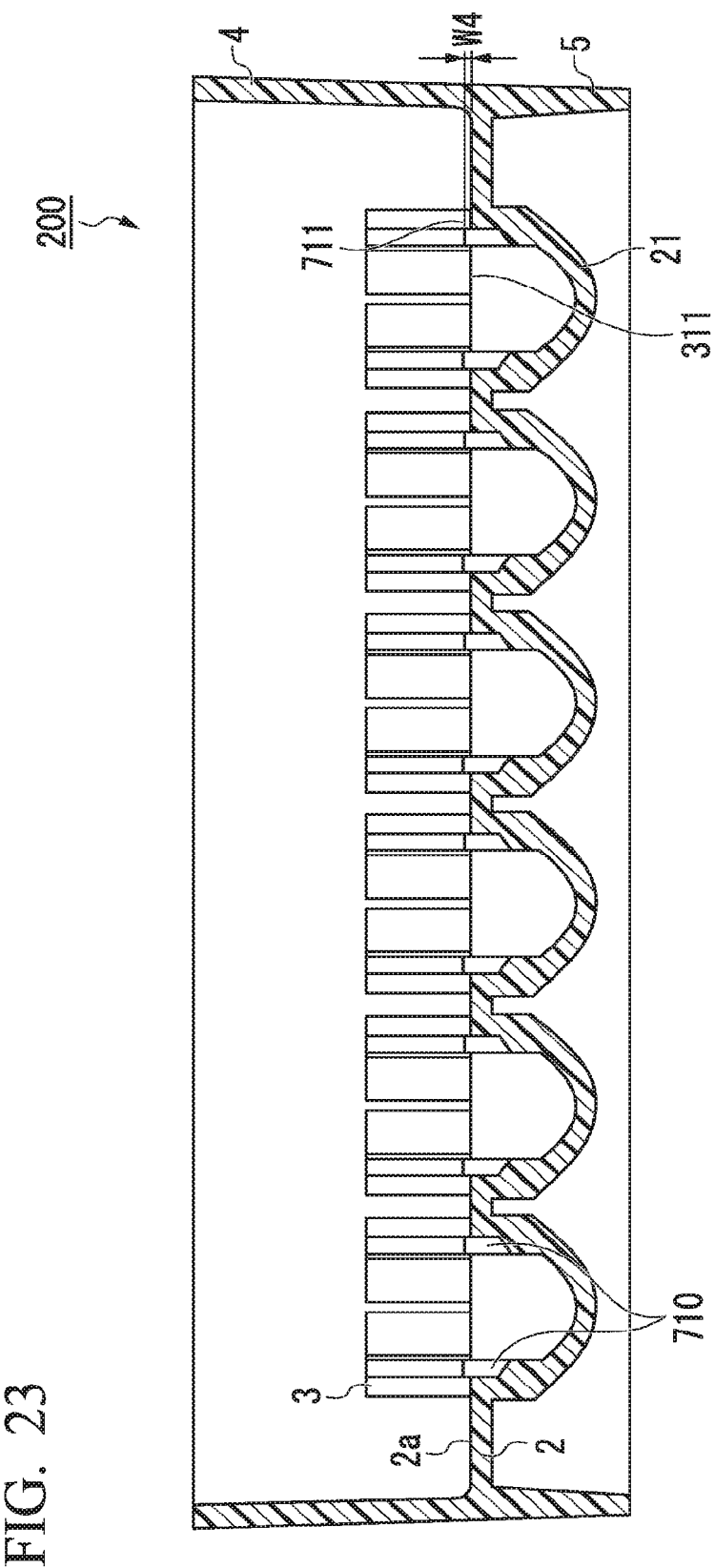
FIG. 23 is an enlarged sectional view in the direction of arrow line XXIII-XXIII' in FIG. 22A.
Figure 24A:
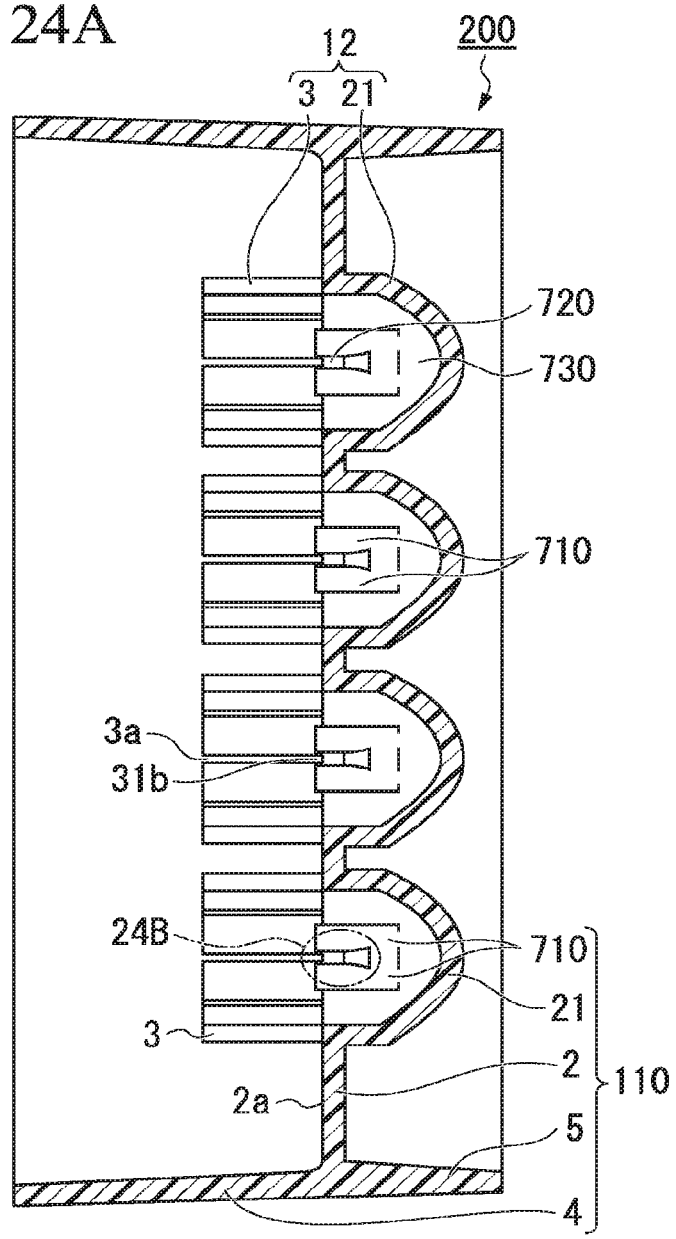
FIG. 24A is an enlarged sectional view in the direction of arrow line XXIV-XXIV' in FIG. 22A.
Figure 24B:
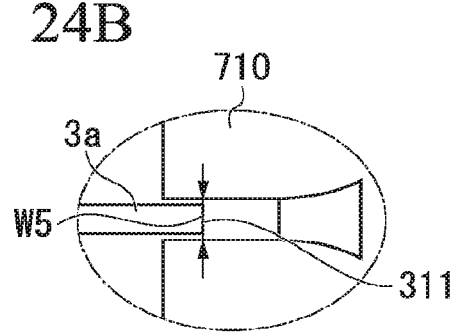
FIG. 24B is a partial enlarged view of FIG. 24A.
Figure 25:
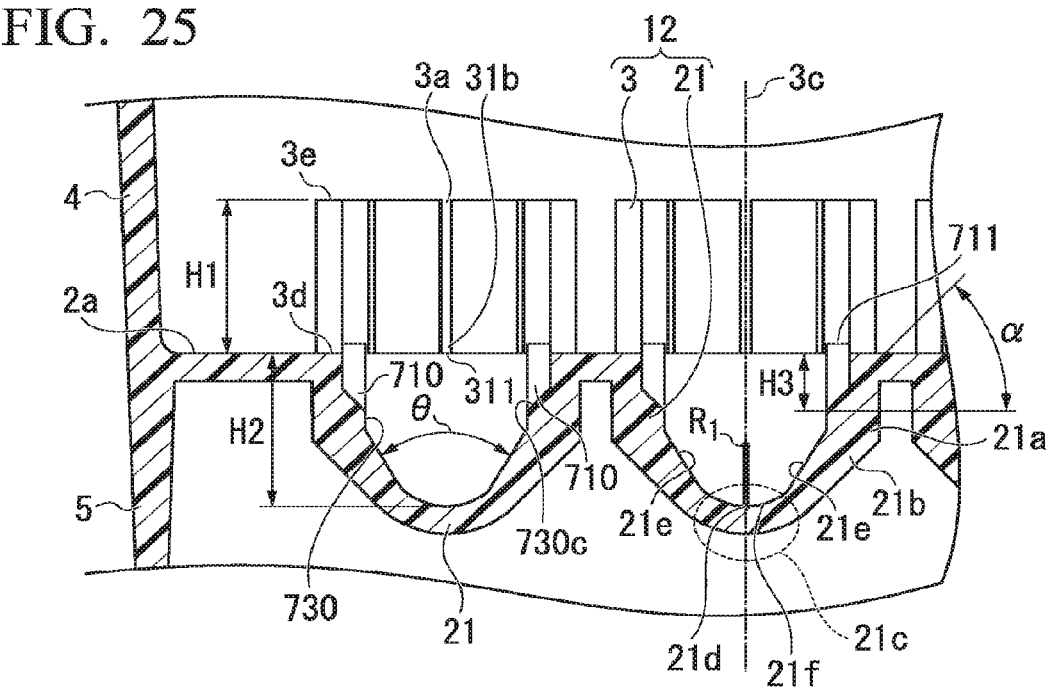
FIG. 25 is a partial enlarged view of FIG. 23.
Figure 26:
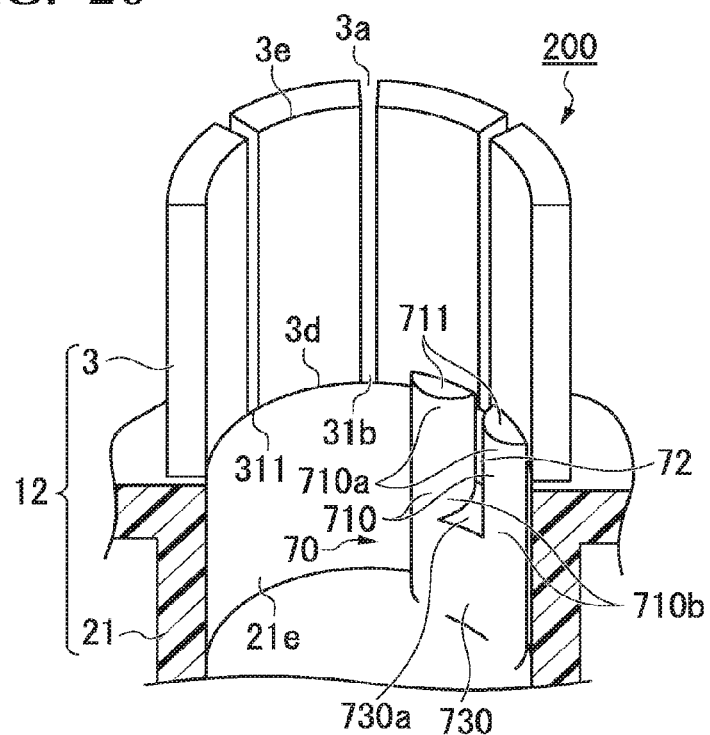
FIG. 26 is a perspective sectional view for describing an internal structure of a structure made up of a tubular body and a well of the cell aggregate culture vessel illustrated in FIG. 22A.
Figure 27:
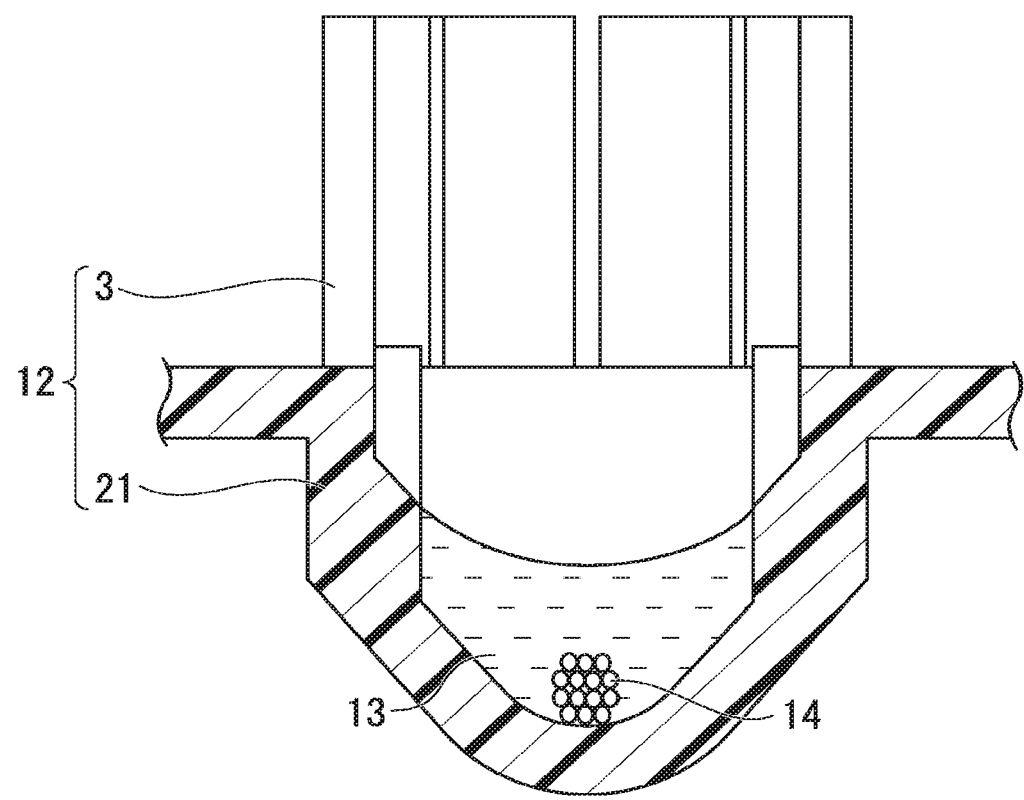
FIG. 27 is a conceptual view for describing a state after cell aggregates are cultured in a culture fluid for a predetermined time using the cell aggregate culture vessel illustrated in FIG. 22A and then some of the culture fluid in the well is discharged.

FIG. 22A is a plan view of a cell aggregate culture vessel 200 of Embodiment 4, and FIG. 22B is a partial enlarged view of FIG. 22A. FIG. 23 is an enlarged sectional view in the direction of arrow line XXIII-XXIII' in FIG. 22A. FIG. 24A is an enlarged sectional view in the direction of arrow line XXIV-XXIV' in FIG. 22A, and FIG. 24B is a partial enlarged view of FIG. 24A. FIG. 25 is a partial enlarged view of FIG. 23, and FIG. 26 is a perspective sectional view for describing an internal structure of the structure 12 made up of the tubular bodies 3 and the wells 21 of the cell aggregate culture vessel 200. FIG. 27 is a conceptual view for describing a state after the cell aggregate 14 is cultured in the culture fluid 13 for a predetermined time using the cell aggregate culture vessel 200 of the present disclosure and then some of the culture fluid in the wells 21 is discharged.

The culture vessel 200 of Embodiment 4 which will be described using FIGS. 22A to 27 has the same constitution as that of the cell aggregate culture vessel 100 of Embodiment 3 except for the fact that the form of the liquid guide portion is different.

The culture vessel 200 of Embodiment 4, similar to the culture vessel 100 of Embodiment 3, includes a plurality of the wells 21 formed in the plate-like body 2, the tubular bodies 3 disposed above the respective wells 21, the side wall 4 which protrudes above the openings of a plurality of the wells 21 and surrounds a plurality of the wells 21, the base 5 which protrudes below the openings of a plurality of the wells 21, and liquid guide portions 70 formed on the inner surface of the structure 12 made up of the tubular bodies 3 and the wells 21. As is clear from FIG. 26, the liquid guide portion 70 includes a liquid guide assisting groove 720 formed by a pair of protrusion portions 710 formed on the inner surface of the structure 12. The liquid guide assisting groove 720 is provided by forming a pair of the protrusion portions 710 on the inner surface of the structure 12 so that upper side end surfaces 711 of the respective protrusion portions 710 are disposed above the lower side ends 311 of the slits 3a and forming the protrusion portions 710 along the same direction as the longitudinal direction of the respective slits 3a on both sides of at least one slit 3a in the width direction in the inner surface of the structure 12 made up of the tubular bodies 3 and the wells 21. In the culture vessel 200 in which the slits 3a are formed from the base ends 3d of the tubular bodies 3, upper side end portions 710a of the respective protrusion portions 710 and the lower side end portions 31b of the slits 3a are disposed at the same positions in the vertical direction.

However, in the culture vessel 200 of Embodiment 4, lower side end portions 710b (refer to FIG. 26) of a pair of the protrusion portions 710 do not reach the bottom surface in the inner surface of the well 21, and the liquid guide portion 70 includes a base portion 730 connecting the lower side end portions 710b of the respective protrusion portions 710 together. Since the base portion 730 is disposed between the bottom surface of the well 21 and a pair of the protrusion portions 710 so as to connect the lower side end portions 710b of the respective protrusion portions 710 together, the base portion 730 has a surface 730a defining one terminating end (closed end) of the liquid guide assisting groove 720. In the culture vessel 200, since the lower side end portions 710b of a pair of the protrusion portions 710 do not reach the bottom portion in the inner surface of the well 21, excessive discharge of culture fluids in the wells 21 to the outside of the structure 12 is suppressed more than in the culture vessel 100 of Embodiment 3 in which the lower side end portions 710b of a pair of the protrusion portions 710 reach the bottom portion in the inner surface of the well 21. Therefore, in the culture vessel 200, it is easy to control the discharge amount of culture fluids, and it is possible to suppress cell aggregates being exposed from culture fluids due to the excessive discharge of culture fluids and thus being damaged.

The surface 730a defining one terminating end (closed end) of the liquid guide assisting groove 720 is preferably an inclined surface 730c inclining downward from the upstream side to the downstream side of the flow of culture fluids capable of flowing into the culture spaces from the slits 3a (inclining upwards from the downstream side to the upstream side) since the inflow of culture fluids is accelerated. As is clear from FIG. 25, the inclined surface 730c inclines downwards from the inner surface (cylindrical surface) of the trunk portion 21a of the well 21 toward the central axis of the well 21. Furthermore, in the present disclosure, the surface 730a defining one terminating end (closed end) of the liquid guide assisting groove 720 may be, for example, a plane parallel to a plane intersecting the central axis of the well 21 at right angles.

The inclination angle α (refer to FIG. 25) of the surface 730a defining one terminating end (closed end) of the liquid guide assisting groove 720 with respect to the plane intersecting the central axis 3c (refer to FIG. 25) of the tubular body 3 at right angles is preferably 0 degrees or more and more preferably 30 degrees or more since the inflow of culture fluids becomes more favorable and is preferably 75 degrees or less and more preferably 60 degrees or less since excessive discharge of culture fluids is suppressed.

In the culture vessel 200 of Embodiment 4 described using FIGS. 22A to 27, the communication portions 3a capable of discharging culture fluids in the wells 21 to the outside of the tubular bodies 3 are slits which are formed in the tubular walls 3b of the tubular bodies 3 and are parallel to the central axes of the tubular bodies 3; however, in the present disclosure, the communication portions 3a are not limited to slits, and, for example, the communication portions may be through-holes which penetrate the tubular walls of the tubular bodies in the thickness directions.

In the culture vessel 200 of Embodiment 4 described using FIGS. 22A to 27, the number of the communication portions 3a, the width W1 of the communication portion 3a, the form of the communication portion 3a, the height H1 of the tubular body 3, the form of the well 21, the depth H2 of the well 21, the capacity of the structure 12, the number of the pairs of the protrusion portions 710, the distance W4 in the vertical direction from the upper side end surface 711 of the protrusion portion 710 to the lower side end 311 of the communication portion 3a, the distance W5 between the protrusion portions 710, the sectional shape of the protrusion portion 710 cut on a surface in a direction intersecting the central axis 3c of the tubular body 3 at right angles, and the like are the same as those in the culture vessel 100 of Embodiment 3. In addition, in the culture vessel 200 of Embodiment 4 as well, similar to the culture vessel 100 of Embodiment 3, the cell adhesiveness reduction treatment is preferably carried out at least on the inner surface of the bottom portion 21b of the well 21.

The cell aggregate culture vessel of the present embodiment, similar to the cell aggregate culture vessel of Embodiment 2, may be constituted of a multi-well plate body and a liquid flow control body. In this case, the cell aggregate culture vessel, similar to the cell aggregate culture vessel of Embodiment 2, can be manufactured by separately molding the multi-well plate body and the liquid flow control body respectively, and, for example, joining these components or disposing the liquid flow control body in the multi-well plate body.

When the culture vessel 200 of Embodiment 4 is used in the above-described "cell aggregate culture method", there is little influence on cell aggregates, and culture fluids can be efficiently exchanged with each other, and thus cell aggregates can be efficiently cultured.

Hereinafter, the present disclosure will be described on the basis of the following examples and comparative examples, but the present disclosure is not limited thereto.

EXAMPLES

Example 1

[Manufacturing of Culture Vessel for Cell Aggregates]

A 24-well multi-well plate (horizontal side: 65.0 mm, vertical side: 50.0 mm, height: 20.5 mm) was molded using a polystyrene resin (manufactured by PS Japan Corporation, trade name: HF77) by means of injection molding. A culture vessel in the present example was provided with a shape illustrated in FIGS. 1A to 3, wells were provided with a shape illustrated in FIG. 4, the aperture angle (θ in FIG. 4) of the bottom surface was set to 85 degrees, and the curvature radius $R_1$ of the inner surface in the bottom portion central portion was set to 2.0 mm. At the opening of each of the wells, the diameter was set to 6.2 mm, and the depth was set to 5.0 mm, and the depth of the trunk portion was set to 2.6 mm. In addition, in each of the tubular bodies, the inner diameter was set to 6.2 mm, the height was set to 5.0 mm, the thickness of the side wall was set to 0.8 mm, and the capacity of a structure made up of the wells and the tubular bodies per inside space was set to approximately 250 μL. In the tubular body, communication portions in which the width W1 of a slit was 0.3 mm were provided at a total of eight places approximately every 45 degrees.

A plasma treatment (oxygen plasma, 10 minutes) was carried out on the 24-well multi-well plate to which the obtained tubular bodies were attached using a plasma treatment device (manufactured by Branson/IPC, SERIES 7000). Therefore, wettability was imparted to the plate surface as a pretreatment.

(Surface Treatment in which Water-Soluble Resins were Used)

Next, in order to carry out a surface treatment on the wells, a polyvinyl alcohol having an azide group in a side chain (manufactured by Toyo Gosei Co., Ltd., azide-unit pendant water soluble photopolymer (AWP, r1=1 to 1,000, r2=4 to 4,995, r3=0 to 4,000, n=1, 2, or 3, R is a group represented by Formula (II) below): a compound represented by Formula (Ia) below (the average degree of polymerization of water-soluble resins: 1,600, the introduction ratio of photosensitive groups: 0.65 mol %)) as a water-soluble resin was dissolved in an aqueous solution of 25% by volume of ethanol in a light shield polypropylene vessel dyed with a brown pigment, thereby preparing a solution of 0.5% by weight of a water-soluble resin.

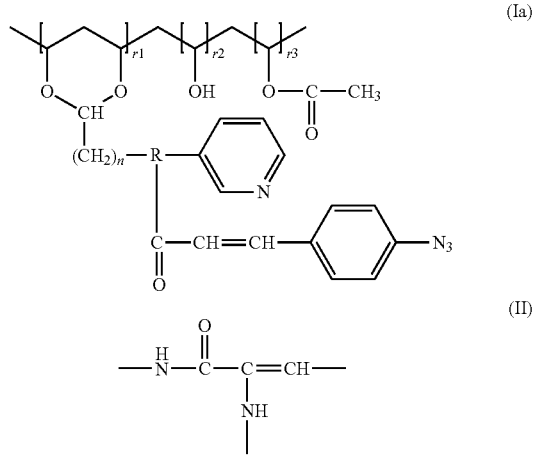

After the above-described solution of 0.5% by weight of a water-soluble resin was added to the plasma-treated plate so that each well contained 50 μL and was left to stand for one minute, the plate was turned over, and a surplus amount of the solution was disposed of. Next, the solution was primarily dried at 40° C. for 60 minutes and then was irradiated with 250 nm UV light using a UV lamp at 1.0 mW/cm$^2$ for 30 seconds, thereby curing the water-soluble resin. Next, the plate was repeatedly washed three times using ultrapure water, was dried, and then was irradiated with y rays at an absorbed dose of 10 kGy (a device manufactured by Radia Industry Co., Ltd.), thereby obtaining a culture vessel of Example 1.

[Formation of Cell Aggregates (Spheroids) for which Human Hepatocellular Carcinoma Cells (HepG2) were Used]

A cell suspension obtained by dispersing HepG2 in a culture fluid (Dulbecco's modified MEM+10% by volume of fetal bovine serum) at a concentration of 3×10$^4$ cells/mL was prepared, was dispensed in a PrimeSurface (registered trademark) 96V plate (Sumitomo Bakelite Co., Ltd., MS-9096V) so that each well contained 100 μL, and was cultured in a carbon dioxide culture vessel including 5% carbon dioxide and having a humidity of 99% and a temperature of 37° C. It was confirmed using a microscope that one cell aggregate (spheroid) having a diameter of approximately 700 μm was formed in each well after six days.

24 Cell aggregates out of cell aggregates having a diameter of approximately 700 μm which had been formed in the respective wells of the PrimeSurface (registered trademark) 96V plate (Sumitomo Bakelite Co., Ltd., MS-9096V) were suctioned at 90 μL/well together with the culture fluid using an ART200G pipette tip (MBP, 2069G), were put into individual wells in the culture vessel of Example 1 together with the culture fluid, then, 1.84 mL of a culture fluid (Dulbecco's modified MEM+10% by volume of fetal bovine serum) was added thereto, the amount of the culture fluid in the entire culture vessel was set to 4 mL, and the cell aggregates were cultured in a carbon dioxide culture vessel including 5% carbon dioxide and having a humidity of 99% and a temperature of 37° C. for three days. Next, the culture vessel of Example 1 was inclined in a variety of directions, some of the culture fluid in the respective wells was collected at the corners of the culture vessel, approximately 3 mL of the culture fluid was suctioned using an aspiration pipette, and then approximately 3 mL of a new culture fluid (fresh culture fluid) was put into the culture vessel of Example 1. Afterwards, culture fluids were exchanged with each other every three days by means of the same operation. During the exchange of culture fluids, attention was paid to prevent the cell aggregates from being dried. After the exchange operation of culture fluids was carried out five times, and cell aggregates in the respective wells were observed using a microscope. As a result, it was found that cell aggregates in all the wells smoothly grew, and the diameters of cell aggregates were 1,100 μm on average.

Comparative Example 1

According to the [formation of cell aggregates (spheroids) for which human hepatocellular carcinoma cells (HepG2) were used] of Example 1, 96 cell aggregates (spheroids) having a diameter of approximately 700 μm were formed. Next, cell aggregates in the respective wells were collected together with a culture fluid in the same manner as in Example 1 and were moved into four PrimaSuface 60 mm Schales (MS-9060X, Sumitomo Bakelite Co., Ltd.) (24 cell aggregates per plate). After the cell aggregates (spheroids) in all the 96 wells were moved to the Schales, 1.84 mL of a new culture fluid was added to each Schale, thereby setting the amount of the culture fluid in the Schale to 4 mL.

After the cell aggregates (spheroids) were moved to the Schales, the culture fluid was exchanged with another three days later. For the exchange of the culture fluids, the Schales were inclined, the cell aggregates were collected at the corners of the Schales, then, 3 mL of the supernatant of the culture fluid was suctioned, and then 3 mL of a new culture fluid was added to the Schales. After the exchange of the culture fluids, the Schales were shaken, and the cell aggregates were dispersed in the culture fluid. Afterwards, culture fluids were exchanged with each other every three days by means of the same operation. As a result of carrying out the exchange operation of culture fluids five times for the four Schales, nine cell aggregates were lost due to the suctioning using a pipette during the exchange operation of culture fluids carried out five times, and, out of the remaining cell aggregates, 28 cell aggregates joined together, and 59 cell aggregates could be cultured as a single independent cell aggregate.

From the above-described results, it became clear that the culture vessel of Example 1 had little influence on cell aggregates and was capable of efficiently exchanging culture fluids and smoothly growing all of the 96 cell aggregates. On the other hand, in the culture vessel of Comparative Example 1, due to the erroneous suction of cell aggregates or the joining between cell aggregates, it was not possible to smoothly grow all of the 96 cell aggregates.

Example 2

[Manufacturing of Culture Vessel for Cell Aggregates]

A 24-well multi-well plate (horizontal side: 65.0 mm, vertical side: 50.0 mm, height: 20.5 mm) was molded using a polystyrene resin (manufactured by PS Japan Corporation, trade name: HF77) by means of injection molding. A culture vessel in the present example was provided with a shape illustrated in FIGS. 22A to 27, wells were provided with a shape illustrated in FIG. 25, the aperture angle (θ in FIG. 25) of the bottom surface was set to 85 degrees, and the curvature radius $R_1$ of the inner surface in the bottom portion central portion was set to 2.0 mm. At the opening of each of the wells, the diameter was set to 6.2 mm, and the depth was set to 5.0 mm, and the depth of the trunk portion was set to 2.6 mm. In addition, in each of the tubular bodies, the inner diameter was set to 6.2 mm, the height was set to 5.0 mm, the thickness of the side wall was set to 0.8 mm, the capacity of a structure made up of the wells and the tubular bodies per inside space was set to approximately 250 μL, and the capacity of a portion below the lower side ends of the slits in the structure, that is, the capacity of each of the wells was set to approximately 105 μL. In the tubular body, communication portions in which the width W1 (refer to FIG. 22B) of a slit was 0.3 mm were provided at a total of eight places approximately every 45 degrees. In addition, two liquid guide portions were provided in the structure made up of the wells and the tubular bodies. W4 (refer to FIG. 23) was set to 0.3 mm, and W5 (refer to FIG. 24B) was set to 0.5 mm. The inclination angle α (refer to FIG. 25) of a surface defining one terminating end (closed end) of a liquid guide assisting groove was set to 45 degrees, and the length H3 (refer to FIG. 25) of the liquid guide assisting groove in the vertical direction in the well was set to 1.5 mm. The shape of a cut surface of a protrusion portion cut in a surface in a direction intersecting the central axis of the tubular body at right angles was substantially an arch (a shape regulated by an overlapping portion of two circles), and a curved line which constituted the arch and protruded in a direction of the central axis of the tubular body was a part of a circumference which had the center that passed through the center of the slit in the width direction and was on a tangent line of a circumference including the inner surface of the tubular body and a curvature radius $R_2$ (refer to FIG. 20) of 0.7 mm.

A plasma treatment (oxygen plasma, 10 minutes) was carried out on the 24-well multi-well plate to which the obtained tubular bodies were attached using a plasma treatment device (manufactured by Branson/IPC, SERIES 7000). Therefore, wettability was imparted to the plate surface as a pretreatment.

(Surface Treatment in which Water-Soluble Resins were Used)

Next, a surface treatment was carried out on the wells in the same manner as for the culture vessel of Example 1, thereby obtaining a culture vessel of Example 2.

Example 3

A culture vessel of Example 3 was produced in the same manner as in Example 2 except for the fact that the inclination angle α was set to 0 degrees.

Example 4

A culture vessel of Example 4 was produced in the same manner as in Example 2 except for the fact that H3 was set to 1.0 mm.

Example 5

A culture vessel of Example 5 was produced in the same manner as in Example 2 except for the fact that the inclination angle α was set to 0 degrees, and H3 was set to 0.5 mm.

Example 6

A 24-well multi-well plate (horizontal side: 65.0 mm, vertical side: 50.0 mm, height: 20.5 mm) was molded using a polystyrene resin (manufactured by PS Japan Corporation, trade name: HF77) by means of injection molding. A culture vessel in the present example was provided with a shape illustrated in FIGS. 15A to 21, wells were provided with a shape illustrated in FIG. 18, the aperture angle (θ in FIG. 18) of the bottom surface was set to 85 degrees, and the curvature radius $R_1$ of the inner surface in the bottom portion central portion was set to 2.0 mm. At the opening of each of the wells, the diameter was set to 6.2 mm, and the depth was set to 5.0 mm, and the depth of the trunk portion was set to 2.6 mm. In addition, in each of the tubular bodies, the inner diameter was set to 6.2 mm, the height was set to 5.0 mm, and the thickness of the side wall was set to 0.8 mm, the capacity of a structure made up of the wells and the tubular bodies per inside space was set to approximately 250 μL, and the capacity of a portion below the lower side ends of the slits in the structure, that is, the capacity of each of the wells was set to approximately 105 μL. In the tubular body, communication portions in which the width W1 (refer to FIG. 22B) of a slit was 0.3 mm were provided at a total of eight places approximately every 45 degrees. In addition, two pairs of protrusion portions were provided as liquid guide portions in the structure made up of the wells and the tubular bodies. W4 (refer to FIG. 16) was set to 0.3 mm, and W5 (refer to FIG. 17B) was set to 0.5 mm. The length H3 of the liquid guide assisting groove in the vertical direction in the well was set to 3.52 mm. The shape of a cut surface of a protrusion portion cut in a surface in a direction intersecting the central axis of the tubular body at right angles was substantially an arch (a shape regulated by an overlapping portion of two circles), and a curved line which constituted the arch and protruded in a direction of the central axis of the tubular body was a part of a circumference which had the center that passed through the center of the slit in the width direction and was on a tangent line of a circumference including the inner surface of the tubular body and a curvature radius $R_2$ (refer to FIG. 20) of 0.7 mm. Similar to Example 2, a surface treatment was carried out using a water-soluble resin, thereby producing a culture vessel of Example 6.

Example 7

A culture vessel of Example 7 was produced in the same manner as in Example 4 except for the fact that the number of the liquid guide portions was set to one.

[Evaluation of the Properties of Culture Fluids being Discharged and Flowing In]

For the culture vessels of Examples 1 to 7, the properties of culture fluids being discharged and flowing in were evaluated according to the following methods. First, 6 mL of a culture fluid was added to the inside of the culture vessel placed on a horizontal surface, and the amount of the entire culture fluid in the culture vessel was set to 6 mL. After that, the culture vessel was inclined 20 degrees for five seconds so that the culture fluid was discharged through the slits having the protrusion portions of the liquid guide portions provided on both sides, some of the culture fluid in the respective wells was collected at the corners of the culture vessel, immediately, approximately 5 mL or more (5.2 mL to 5.9 mL) of the culture fluid was suctioned using an aspiration pipette, and the inclination of the culture vessel was returned to zero degrees after the suction. After that, the amount of the culture vessel remaining in the respective wells was collected and measured using a micro pipette, the property of the culture fluid being discharged was evaluated on the basis of the following "evaluation standard 1", and the results are shown in Table 1. After that, approximately 5 mL of a fresh culture fluid was put into the corners of the culture vessel, was left to stand for 10 seconds, and then the culture fluid in the respective wells was observed. In addition, the properties of the culture fluid flowing into the wells were evaluated on the basis of the following "evaluation standard 2", and the results are shown in Table 1.

[Evaluation Standard 1]

A: The amount of the culture fluid remaining in the wells is 1/15 or greater and 1/4 or smaller of the well capacity (105 µL).

13: The amount of the culture fluid remaining in the wells is smaller than 1/15 of the well capacity (105 µL).

C: The amount of the culture fluid remaining in the wells exceeds 1/4 of the well capacity (105 µL).

[Evaluation Standard 2]

A: The culture fluid flows into the wells, the culture fluid surface in the culture vessel was above the lower side ends of the slits, and the culture fluid surface in the structure made up of the wells and the tubular bodies is present on the same plane as the culture fluid surface in portions other than the structure.

B: The culture fluid does not flow into the wells, the culture fluid surface in the wells was below the lower side ends of the slits, and the culture fluid surface is lower in the structure made up of the wells and the tubular bodies than in portions other than the structure.

TABLE 1

| | Number of liquid guide portions | H3 (mm) | Inclination angle α (degrees) | Property of culture fluid being discharged | Property of culture fluid flowing in |
|---|---|---|---|---|---|
| Example 1 | 0 | No liquid guide portion | No liquid guide portion | C | B |
| Example 2 | 2 | 1.5 | 45 | A | A |
| Example 3 | 2 | 1.5 | 0 | A | A |
| Example 4 | 2 | 1.0 | 45 | A | A |
| Example 5 | 2 | 0.5 | 0 | A | A |
| Example 6 | 2 | 3.52 | N/A | B | A |
| Example 7 | 1 | 1.0 | 45 | A | A |

As shown in Table 1, it has been clarified that, in the culture vessels of Examples 2 to 7 in which the liquid guide portions were provided, compared with the culture vessel of Example 1 in which the liquid guide portions were not provided, the property of culture fluids being discharged and the property of culture fluids flowing in were more favorable. Therefore, in the culture vessels of Examples 2 to 7, compared with the culture vessel of Example 1, it is possible to more efficiently exchange culture fluids.

INDUSTRIAL APPLICABILITY

The present disclosure is useful in, for example, medical fields such as studies of human ES cells and regenerative medicine.

The present invention can also be carried out in forms other than what has been described above within the scope of the gist of the present invention. Embodiments disclosed in the present application are examples, and the present invention is not limited thereto. The scope of the present disclosure is preferentially interpreted on the basis of the description of the accompanying claims rather than the description of the above-described specification, and all modifications within ranges equivalent to the claims are considered to be within the claims.

REFERENCE SIGNS LIST 1, 6, 100, 200 . . . cell aggregate culture vessel, 2, 7 . . . plate-like body, 21, 71 . . . well, 21a . . . trunk portion, 21b . . . bottom portion, 21c . . . central portion of bottom portion, 21d . . . top point (deepest portion) of inner surface of well, 21c . . . inner surface (inclined surface) of well, 3, 81 . . . tubular body, 3c, 81a . . . central axis of tubular body, 3a . . . slit (communication portion), 4, 9 . . . side wall, 9a . . . inner surface of side wall, 5, 10 . . . base, 11, 61 . . . multi-well plate body, 80 . . . connected body, 800 . . . liquid flow control body, 82 . . . crosslinking portion, 83 . . . position-regulating portion, 81b . . . communication portion (slit), 84b . . . groove, 60, 70 . . . liquid guide portion, 610, 710 . . . protrusion portion, 620, 720 . . . liquid guide assisting groove, 730 . . . base portion

The invention claimed is:

1. A culture vessel for culturing a cell aggregate, comprising:
   a plate body having a plane;
   a plurality of wells each having an opening formed at the plane of the plate body and a culture space configured to store a cell aggregate and culture fluid;
   a plurality of tubular bodies formed on the plane of the plate body such that each of the plurality of tubular bodies is attached to and projecting upward from the plane of the plate body and has an inner cavity communicating with the culture space of a respective one of the plurality of wells through the opening; and
   a side wall formed on the plate body and positioned outside the plurality of tubular bodies such that the side wall is projecting upward from the plane of the plate body and surrounding the plurality of wells,
   wherein each of the plurality of tubular bodies has a tubular wall having at least one communication portion such that the at least one communication portion forms at least one communication opening through which the culture fluid is discharged from the plurality of tubular bodies into a space formed between the plurality of tubular bodies and a space formed between the tubular wall and the side wall without allowing passage of the cell aggregate, and that the at least one communication opening has one end at the plane of the plate body.

2. The culture vessel according to claim 1, wherein the at least one communication portion comprises a plurality of communication portions formed in each of the plurality of tubular bodies.

3. The culture vessel according to claim 1, wherein the at least one communication portion is a slit formed parallel to a central axis of a respective one of the plurality of tubular bodies.

4. The culture vessel according to claim 1, wherein the at least one communication portion is a slit formed along a circumferential direction of a respective one of the plurality of tubular bodies.

5. The culture vessel according to claim 3, wherein the slit has a width which is in a range of from 0.1 mm to 0.5 mm.

6. The culture vessel according to claim 3, wherein the slit is formed such that a length H2 from an end of the slit at the plane of the plate body to a deepest portion of a respective one of the plurality of wells is in a range of from 3.0 mm to 6.0 mm.

7. The culture vessel according to claim 1, wherein the plate body and the plurality of wells form an integral structure comprising resin material.

8. The culture vessel according to claim 7, wherein the at least one communication portion is a slit which is formed parallel to a respective one of central axes of the plurality of tubular bodies and extends from a base end of a respective one of the plurality of tubular bodies.

9. The culture vessel according to claim 7, wherein the plate body and the plurality of tubular bodies are molded in a same mold.

10. The culture vessel according to claim 1, further comprising:
a plurality of crosslinking portions connecting the plurality of tubular bodies such that the plurality of crosslinking portions do not to come into contact with the plate body; and
a pair of position-regulating portions each comprising a pair of bodies each having two end portions formed such that a first one of the position-regulating portions in the pair has one of the two end portions connected to one of the plurality of tubular bodies and an opposite one of the two end portions connected to a first inner surface of the side wall and that a second one of the position-regulating portions in the pair has one of the two end portions connected to one of the plurality of tubular bodies and an opposite one of the two end portions connected to a second inner surface of the side wall on an opposite side of the first inner surface of the side wall,
wherein the side wall has a substantially rectangular shape surrounding the plurality of wells.

11. The culture vessel according to claim 10, wherein the plurality of tubular bodies and the plurality of crosslinking portions form a liquid flow control body that is a separate body from the plate body.

12. The culture vessel according to claim 1, further comprising:
a liquid guide portion comprising a pair of protrusion portions formed on an inner surface of a structure comprising each of the plurality of wells and a respective one of the plurality of tubular bodies such that the protrusion portions in the pair form a liquid guide assisting groove and have upper side end surfaces positioned above a lower side end of the at least one communication portion.

13. The culture vessel according to claim 12, wherein the protrusion portions in the pair facing the culture space have curved surfaces protruding toward a central axis of a respective one of the plurality of tubular bodies.

14. The culture vessel according to claim 12, wherein a length from the upper side end surfaces of the protrusion portions in the pair to the lower side end of the at least one communication portion is at least 0.1 mm.

15. The culture vessel according to claim 12, wherein a distance between the protrusion portions in the pair on a circumference passing through the lower side end of the at least one communication portion is in a range of from 0.3 mm to 1.0 mm.

16. The culture vessel according to claim 12, wherein the protrusion portions in the pair have lower side end portions that reach a bottom surface in an inner surface of a respective one of the plurality of wells.

17. The culture vessel according to claim 12, wherein the liquid guide portion has a base portion formed such that the protrusion portions in the pair have lower side end portions connected to the base portion including a surface defining a terminating end of the liquid guide assisting groove.

18. The culture vessel according to claim 17, wherein the surface defining one terminating end of the liquid guide assisting groove is an inclined surface inclining from a downstream side to an upstream side of a flow of the culture fluid flowing from the at least one communication portion into the culture space of each of the plurality of wells.

19. The culture vessel according to claim 12, wherein the liquid guide assisting groove is formed to have a closed end above a bottom portion of a respective one of the plurality of wells.

20. The culture vessel according to claim 1, wherein at least an inner surface of a bottom portion of each of the plurality of wells is coated with a coating layer formed of a water-soluble resin represented by Formula (Ia)

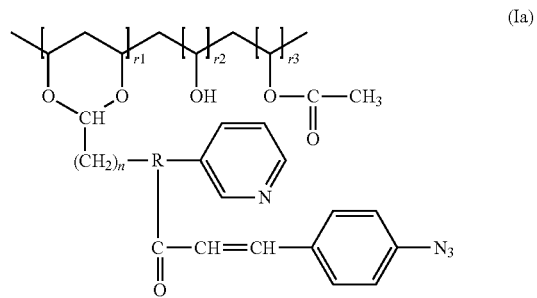

where, R represents a hydrocarbon group having a carbonyl group and a —NH— group, r1 represents 1 to 1,000, r2 represents 40 to 4,995, r3 represents 0 to 4,000, and n represents 1, 2, or 3
or Formula (Ib),

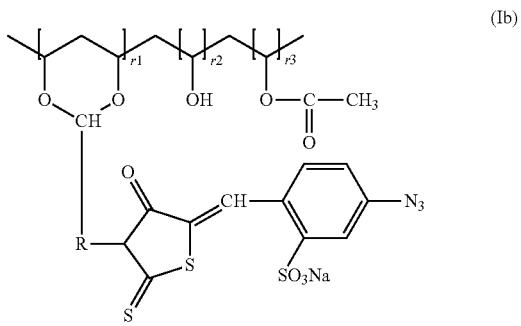

where, R represents a hydrocarbon group having a carbonyl group and a —NH— group, r1 represents 1 to 1,000, r2 represents 40 to 4,995, and r3 represents 0 to 4,000.

21. The culture vessel according to claim 1, wherein each of the plurality of wells has a tubular trunk portion and a funnel-shaped bottom portion formed at one end of the tubular trunk portion, a central portion of the funnel-shaped bottom portion is a concave surface, an aperture angle of the funnel-shaped bottom portion is in a range of 60 degrees to 100 degrees, and a curvature radius of the concave surface of the funnel-shaped bottom portion is in a range of 0.5 mm to 2.0 mm.

22. The culture vessel according to claim 1, wherein the cell aggregate is stem cells.

23. The culture vessel according to claim 22, wherein the stem cells are human embryonic stem cells, human pluripotent stem cells, or human iPS cells.

24. A cell aggregate culture method for culturing a cell aggregate, comprising:
- culturing a cell aggregate in each of the plurality of wells in which the culture space is filled with culture fluid in the culture vessel of claim 1; and
- inclining the culture vessel after the culturing, thereby passing part of the culture fluid in each of the plurality of wells through the at least one communication portion and discharging the culture fluid from each of the plurality of tubular bodies.

* * * * *